United States Patent
Pretz et al.

(10) Patent No.: US 9,427,615 B2
(45) Date of Patent: Aug. 30, 2016

(54) KINETIC CHAIN TRAINING SYSTEM

(71) Applicant: VP Innovations, LLC, Poplar Bluff, MO (US)

(72) Inventors: Ryan Russell Pretz, Poplar Bluff, MO (US); Clint Lee Vanlandingham, Poplar Bluff, MO (US)

(73) Assignee: VP Innovations LLC, Poplar Bluff, MO (US)

( * ) Notice: Subject to any disclaimer, the term of this patent is extended or adjusted under 35 U.S.C. 154(b) by 296 days.

(21) Appl. No.: 14/308,001

(22) Filed: Jun. 18, 2014

(65) Prior Publication Data

US 2015/0367158 A1    Dec. 24, 2015

(51) Int. Cl.
| | |
|---|---|
| *A63B 21/00* | (2006.01) |
| *A63B 21/04* | (2006.01) |
| *A63B 21/055* | (2006.01) |
| *A63B 21/16* | (2006.01) |
| *A63B 69/00* | (2006.01) |
| *A63B 23/035* | (2006.01) |

(Continued)

(52) U.S. Cl.
CPC ....... *A63B 21/0442* (2013.01); *A63B 21/0552* (2013.01); *A63B 21/0555* (2013.01); *A63B 21/0557* (2013.01); *A63B 21/065* (2013.01); *A63B 21/16* (2013.01); *A63B 21/169* (2015.10); *A63B 21/4007* (2015.10); *A63B 21/4011* (2015.10); *A63B 21/4013* (2015.10); *A63B 21/4017* (2015.10); *A63B 21/4021* (2015.10); *A63B 21/4025* (2015.10); *A63B 21/4043* (2015.10); *A63B 23/03508* (2013.01); *A63B 23/03516* (2013.01); *A63B 23/03541* (2013.01); *A63B 23/03558* (2013.01); *A63B 24/0075* (2013.01); *A63B 69/002* (2013.01); *A63B 69/0002* (2013.01); *A63B 69/004* (2013.01); *A63B 2069/0006* (2013.01); *A63B 2069/0008* (2013.01)

(58) Field of Classification Search
CPC ...................................................... A63B 21/00
USPC ............................................ 482/51, 52, 121
See application file for complete search history.

(56) References Cited

U.S. PATENT DOCUMENTS

| | | | |
|---|---|---|---|
| 6,945,919 B2 * | 9/2005 | Yang ........................ | A63B 5/11 482/141 |
| 7,494,453 B2 | 2/2009 | Wehrell | |
| 7,625,320 B2 | 12/2009 | Wehrell | |

(Continued)

*Primary Examiner* — Jerome W Donnelly
(74) *Attorney, Agent, or Firm* — Don V. Kelly; Evans & Dixon, L.L.C.

(57) ABSTRACT

A training system includes a panel upon which a plurality of anchors are disposed. The anchors are adapted to connect to the proximal end of a resistance line, the distal end of each resistance line is attached to a user training a specific movement. The system includes a computer in electronic communication with a printer. The computer receives dimensional information for a particular user and instructs a printer to print a sheet. The sheet is adapted to overlay and be held by the panel. The anchors are accessible through the sheet. The printing on the sheet contains indication for the user of groupings of anchors to which to attach resistance lines to train a particular sport-specific movement. In an alternate embodiment, the computer is in electronic communication with a projector. The computer receives dimensional information for a particular user and instructs the projector to project a display on the panel. The display contains indication for the user of groupings of anchors to which to attach resistance lines to train a particular sport-specific movement.

16 Claims, 23 Drawing Sheets

(51) Int. Cl.
*A63B 21/065* (2006.01)
*A63B 24/00* (2006.01)

(56) References Cited

U.S. PATENT DOCUMENTS

| | | | |
|---|---|---|---|
| 7,651,450 B2 | 1/2010 | Wehrell | |
| 8,512,142 B2* | 8/2013 | Meldeau | A63B 23/0458 463/36 |
| 8,986,165 B2* | 3/2015 | Ashby | A63B 24/0087 482/1 |
| 2004/0087418 A1* | 5/2004 | Eldridge | A63B 21/157 482/54 |
| 2006/0229167 A1* | 10/2006 | Kram | A63B 21/4015 482/54 |
| 2008/0300118 A1 | 12/2008 | Wehrell | |
| 2010/0130338 A1 | 5/2010 | Wehrell | |
| 2013/0130866 A1 | 5/2013 | Wehrell | |

* cited by examiner

KINETIC CHAIN TRAINING SYSTEM

CROSS REFERENCE TO RELATED APPLICATION

Not applicable.

STATEMENT REGARDING FEDERALLY SPONSORED RESEARCH OR DEVELOPMENT

Not applicable.

SEQUENCE LISTING, TABLE OR COMPUTER PROGRAM ON COMPACT DISC

Not applicable.

FIELD OF INVENTION

This invention relates to athletic training devices designed to impart resistance to sport-specific movements.

BACKGROUND OF THE INVENTION

Athletic movements like throwing and kicking, though ostensibly involving only a major extremity, actually involve a complex interaction of a multitude of muscular and skeletal components across the entirety of the body. These muscular and skeletal components work simultaneously and serially to produce a given body movement. For example, during the action of throwing a baseball, the body will go through a large number of movements that typically begins with the thrower moving the throwing arm backwards relative to the target while simultaneously pulling the opposite leg up and back. From this position, the raised opposite leg is thrust toward the target so as to pull the body toward the target. At the same time, the grounded leg drives the body in the same direction. As the body is pulled and driven toward the target, it pulls the throwing arm along with it. The throwing arm is moved at high velocity so that the hand on the arm is, in turn, pulled and snapped like a whip by the throwing arm. The velocity imparted to the hand is transferred to the ball and the ball released while the hand is in motion. The interaction of the muscular and skeletal components during such a process is called the kinetic chain.

Over the past few decades, exercise devices have appeared that are designed to train and strengthen the components of the body used during the sport-specific, complicated movements like throwing or kicking. These devices use oppositional resistance against the body itself or the separate body parts to train the body at speeds akin to those involved in the particular sport-specific movement. For example, several such devices appear in United States Published Patent Application No. 5080300118 ("Wehrell"). These prior art devices, apply one or more lateral resistive loads to participants performing complex motions at low or high speeds. The intent is to condition the body to eventually perform these complex movements at competition speed by applying low-level resistance.

With the prior art device, resistive bands or cables are spooled in mechanical assemblies. The bands or cables emanate from the mechanical assemblies and are fed through pulley assemblies that can be located at various vertical or horizontal positions. The ends of the bands or cables include attachment means to allow attachment of the bands or cables to body parts or a harness. For example, as shown in Wehrell FIG. 36, for a person engaged in training a throwing motion, the device will provide for resistive loads to be applied to the wrist, waist and ankles.

Though the prior art devices are highly useful in training the components of the kinetic chain, one deficit of the prior art devices is their complexity. Of note, the devices tend to be complicated devices having the bands or cables ("resistance lines") emanating from mechanical assemblies and fed through independently positionable pulley assemblies. The resistance lines project from these pulley assemblies on the main structure of the device and attach either directly to a body part on the user or to a garment worn by the user. To properly employ the device, the person setting up the device (which could be the athlete user, but is more typically a trainer training the athlete) must select resistance lines of the proper length and resistance to attach to the several body parts or the garment.

In addition to selecting the proper lengths and resistances for the resistance lines, the person adjusting the device will need to select the proper origin point for the resistance lines. For example, in the Wehrell device the positioned pulley assemblies can be slidably moved along rails or positioned on a peg board surface and locked into place. Once locked, the positioned pulley assemblies represent an effective origin point for the cable or band leading to the body part of the user.

One deficit with the prior art device is that it offers the user a daunting number of options of where to position the origin points. However, it has been shown that to properly train the body parts involved in a kinetic chain movement, the resistive force applied to a body part should emanate from a localized area so that involved muscles receive optimal loading and involved ligaments and tendons are not dangerously torqued or stressed by application of misdirected loading. For example, in the case of a pitching movement, if the load applied to the forearm on the throwing arm emanates from too high or low of an origin point, the elbow and wrist joints can be improperly leveraged, which can result in counter-productive injury to the user. Similarly, another deficit of the prior art device is that it does not cue the user on how to perform a particular exercise. Of particular usefulness to the user is an indication of the body position to assume when initiating resistance training for a sport-specific movement.

SUMMARY OF THE INVENTION

The instant invention addresses the deficits of the prior art device by providing for a kinetic chain training system that provides for the application of resistive loads to a plurality of body parts of a user involved in a particular sports movement, such as throwing a ball, hitting a baseball or kicking a ball, based upon the user's individual body dimensions. In contrast to the prior art, the system provides indication to the user of the optimal anchor points for the bands providing the resistive loading based upon the user's size dimensions. The present invention provides this indication through a variety of embodiments. By virtue of this user instruction the present invention system provides optimally positioned resistance loading to the anatomy of a user engaged in a sport-specific bodily movement.

A first embodiment of the present invention system includes a panel. The panel includes one or more mechanical fastener elements that allow the panel to be removably secured, directly or indirectly to a wall or frame. The panel has a front surface. A plurality of anchors are disposed in a pattern across the front surface of the panel. The system further includes a plurality of elastic resistance lines. Each elastic resistance line has a proximal end and a distal end. The distal end of each elastic resistance line is adapted to removably connect to one or more locations on the user's body. Preferably the distal end of each elastic resistance line includes a sizeable loop (i.e., a belt or cuff) that may be cinched to the limbs or trunk of a user body. Alternatively, the resistance line may be include a mechanical fastener, such as a carabiner or clip that can attach to a cuff, bracelet, belt or harness worn by the user.

The proximal end of each elastic resistance line is adapted to removably connect to one or more of the plurality of anchors. Each anchor is shaped to receive (connect to) the proximal end of an elastic resistance line. Thus, the shape and mechanical function of each anchor will depend upon the type of connector desired for the proximal end of the resistance line which will attach to it. A variety of differing end treatments for a resistance line may be used.

The first embodiment system further comprises a computer and a printer. The printer is in electronic communication with the computer. The computer is programmed to accept dimensional information about the athlete and then communicate with a large printer to print a sheet that can be affixed to the panel. More specifically, the computer is programmed to: a) receive input as to a user's body dimensions and the particular body movement engaged in by the user; b) determine one or more anchor groupings; and c) output a signal to the printer instructing the printer to print a sheet. An anchor grouping defines one or more anchors on the panel. The dimensional information includes at least the user's height and more preferably one or more of the following parameters weight, width, girth, arm and leg length and whether the user is right or left handed and which limb is being trained. As noted, the computer is programmed to use the described input to determine an anchor grouping. As used in this application "determining an anchor grouping" means using the computer input to determine the anchor or anchors on the panel that should connect to a resistance line that is attached to a specific location (e.g., thigh, ankle, waist, wrist, upper arm) on the user's body to properly train the user in a particular body movement (e.g, a sport-specific body movement). Thus, determining an anchor grouping involves determining an area on the panel that should receive a resistance line attached to a specific location on the user's body. Based upon that determination, the computer outputs a signal to the printer instructing the printer to print demarcated areas on a large sheet. As explained below, each demarcated area on the sheet identifies one of the one or more anchor groupings determined by the computer to receive a resistance line.

The printed sheet is adapted to be overlaid or attached to the panel. When the sheet is overlaid on the panel, each demarcated area on the sheet thus defines one of the anchor groupings determined by the computer. Each anchor in an anchor grouping is an anchor to which the proximal end of a resistance line that is attached to a specific location on the user may attach while the user is engaged in the particular body movement. For simplicity of language, rather than continually refer to the connection to an anchor in a grouping, the concept of "connecting to an anchor grouping" means in this application to connect to one of the anchors within an anchor grouping.

Each demarcated area on the printed sheet includes holes that allow access through the sheet so as to allow each anchor in an anchor grouping (defined by the printed demarcated area) to connect to a resistance line attached to the user when the sheet is in the overlaid position. For the user's or trainer's benefit the printed sheet identifies for each demarcated anchor grouping the specific location on the user at which the distal end of a resistance line connected to that anchor grouping should connect while the user is engaged in the particular body movement.

Each printed sheet is sized so as to enable the sheet to overlay the front surface of the panel. The panel removably secures the sheet while the sheet is in the overlaid position. The printed sheet also includes perforations (anchor access holes) which are arranged in a pattern on the sheet that matches the pattern of anchors on the panel. While the sheet is in the overlaid position, its access holes allow access to the demarcated anchor groupings on the panel through the sheet. Thus, users can access each anchor in an anchor grouping to connect to a resistance line.

Text or imagery on the sheet identifies for each resistance line attached to the user the anchor grouping to which the resistance line should connect while the user is engaged in the particularized body movement. A preferred embodiment sheet depicts this information graphically via a printed human form image. The human form image graphically depicts a human form image in a position identifiable with the sport-specific movement being trained. More preferably, the human form image also depicts the starting position the user should assume to begin resistance training for the subject sport-specific movement. Each printed sheet is printed specific to a user training a sport-specific movement and having specific dimensions. The computer is programmed to instruct the printer to print sheets depicting a position identifiable with a different sport-specific movement.

In a second embodiment, a present invention system includes the described panel, the plurality of resistance bands, a computer and projector. This system employs the panel and resistance lines of the first embodiment system. The computer is programmed to receive input regarding, or is adapted to self-determine through positional sensors, the relative location of the projector vis a vis the panel. Once that relative location is established, which in the physical therapy setting is normally not disturbed after being established, the computer can receive input as to user-specific information. The computer is programmed to receive input as to a user's dimensional information and the sport-specific body movement being trained by the user. In this respect the computer hardware or software is designed to accept the same dimensional information about the athlete as in the first embodiment system and then communicate with the projector. More specifically, the computer is programmed to: 1) receive input as to a user's body dimensions and the particular body movement engaged in by the user; 2) determine one or more anchor groupings (each anchor grouping defining one or more anchors on the panel); and 3) output a signal to the projector instructing the projector to project an image on the panel.

With this second embodiment, the dimensions of the user are fed into the computer along with indication of the sport-specific movement being trained. Based upon this information, the computer generates a signal instructing the projector to display imagery on the panel that identifies for a specific user engaging in a particular body movement one or more anchor groupings on the panel that should connect to resistance lines attached to specific locations on the user's body. The projected image includes one or more projected demarcated areas. Each demarcated area defines a grouping of anchors determined by the computer to connect to a resistance line attached to a specific location on the user's body. The projected image may be verbal, graphic or a combination of both.

Preferably, the projector will achieve the desired display by projecting a life-size human form image on the panel. This image projected on the panel includes not just a human form image, but also indication, via demarcated areas in the projected display, of which anchors should receive the resistance lines to properly train the subject sport-specific movement for that particularly dimensioned user. In a further refinement of this embodiment, the projected display can include indication of where on the user's body (e.g., throwing arm, opposite leg and trunk) or harness resistance lines should optimally be placed. The location of each demarcated area on the human form image would thus also identify the location on the user's body at which the distal end of a resistance line should connect and the location on the panel at which the proximal end of the same resistance line should connect while the user is engaged in the particular body movement. Exemplary human form images may be projected on the panel that depict body positions for striking, throwing, bat-swinging and ball-kicking.

In a third embodiment system the invention comprises the plurality of resistance bands and includes a computer. This third embodiment also includes a panel in electronic communication with the computer. The computer is programmed to: 1) receive input as to a user's body dimensions and the particular body movement engaged in by the user; 2) determine one or more anchor groupings; and 3) output a signal to the panel causing the activation of indicators for the one or more anchors in each of the one or more anchor groupings. Each anchor grouping defines one or more anchors on the panel and each anchor in an anchor grouping is an anchor to which the proximal end of a resistance line attached to a specific location on the user may attach while the user is engaged in the particular body movement.

In the third embodiment system, the computer is programmed to accept dimensional information about the athlete and then communicate with the panel. More particularly, the panel is adapted to receive output from the computer so as provide visual means to identify for each anchor grouping the specific resistance line connected to the user that should connect to the grouping. In particular, each anchor would have proximate to or integral to it an electric or electronic indicator that is directly or indirectly in communication with the computer. The indicator could be a light, a verbal display, a color change display, electro-magnetic switch or other type of indicator. In response to the input into the computer of the user's dimensional information and indication of what sport-specific activity is being trained, the computer outputs a signal to the panel instructing the panel to turn on the indicators for the anchors in each anchor grouping that should receive the resistance lines.

The third embodiment system includes a display, which could be a computer monitor, screen integrated on the panel or projected image, identifying for each determined anchor grouping a specific resistance line located on the user that should connect to the grouping while the user is engaged in the particular body movement. In a preferred embodiment, the panel serves as a screen upon which is projected an image that identifies where on the user's body or harness resistance lines should optimally be placed. In this last-mentioned embodiment, the projected image would identify for each anchor grouping the specific location on the user at which the distal end of a resistance line connected to the grouping should connect while the user is engaged in the particular body movement. Even more preferably, the projected image depicts a human form image. The human form image defines an area containing the one or more anchor groupings. The location of each anchor grouping within the human form image identifies the location on the user's body at which the distal end of a resistance line connected to the anchor grouping should connect while the user is engaged in a particular body movement.

The present invention is particularly useful for training sport-specific punching and kicking movements such as are used in boxing, karate, thai boxing, tae kwan do and mixed martial arts. It is also particularly useful for training throwing movements such as pitching or football throwing movements. The system is also useful for training the bat-swinging movement of baseball and the ball-kicking motions as are employed in soccer and American football. Any of the described embodiment systems may include a harness that is wearable by the user. The harness includes at least one receiver (ring or loop) to which the distal end of a resistance line may attach.

DETAILED DESCRIPTION

The present invention is directed to a kinetic chain training system for providing resistive force to a user. The training system is designed to provide indication to the user or the trainer training the user of the location of optimal resistive loading to the anatomy of a user engaged in a sport-specific bodily movement.

Figure 1:
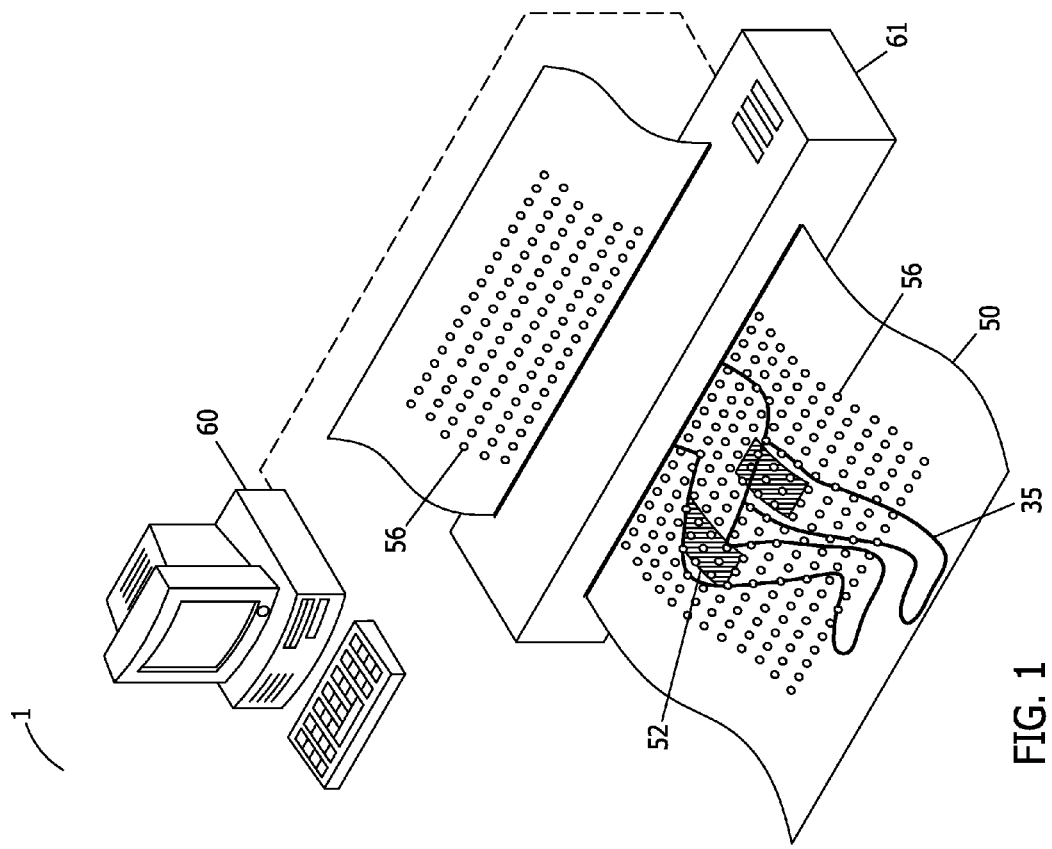
FIG. 1 is a schematic of a first embodiment system that includes a panel, plurality of resistance lines, computer and a large sheet printer.
Figure 1:
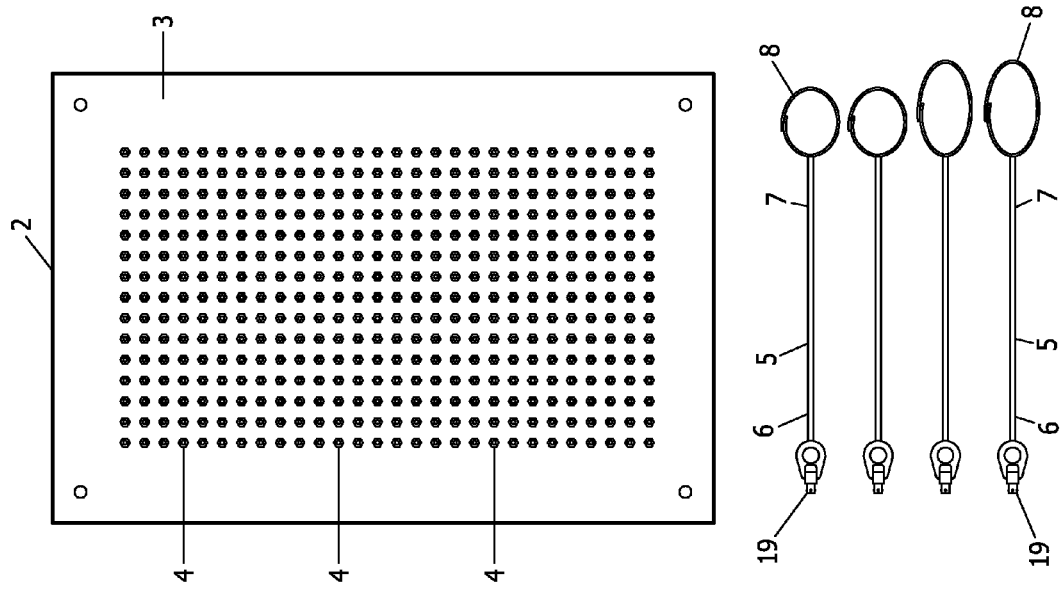

FIGS. 1-4 show features of a first embodiment of the present invention system. As shown in FIG. 1, a first embodiment system includes a panel 2, elastic resistance lines 5, computer 60 and large sheet printer 61. Panel 2 has front surface 3. Panel 2 has a patterned distribution of anchors 4 across its front surface 3. As used herein the word "pattern" or patterned" means that the anchors are arranged in recognizable geometric formations, including but not limited to such patterns as horizontal, vertical or diagonal rows or columns or in concentric circles. Panel 2 may be constructed of thick plywood or other robust material sufficient to accept tension from resistance lines 5 that can attach to anchors 4 on panel 2. System 1 further includes a plurality of elastic resistance lines 5.

The number of resistance lines 5 used with the system will depend upon the sport-specific movement being trained. For example, when configured to train a pitching motion, the apparatus might employ four resistance lines: one for securing to the forearm of the throwing arm of the user; one for securing to the upper portion of the throwing arm; one for securing to the leg opposite that of the throwing arm; and one for securing to the thigh of the planted leg. A user training a soccer or field goal kicking motion might train with resistance lines secured to both lower extremities and the trunk or upper part of the user's body. A martial artist might train with resistance lines secured to the upper trunk, lower trunk and each limb. In other embodiments the resistance lines may be more advantageously connected to the user by way of a harness. Each of the plurality of resistance lines could have the same length or elastic resistance as the other resistance lines. Likely, however, for any given movement being trained, the lengths and resistances of the resistance lines will vary among the plurality of lines. Particularly when included as part of a system, the plurality of resistance lines will include a sub-grouping of resistance lines all having different lengths and a sub-grouping of resistance lines all having different resistances. The sub-groups may overlap in their constituency or may comprise distinct resistance lines.

Figure 5A:
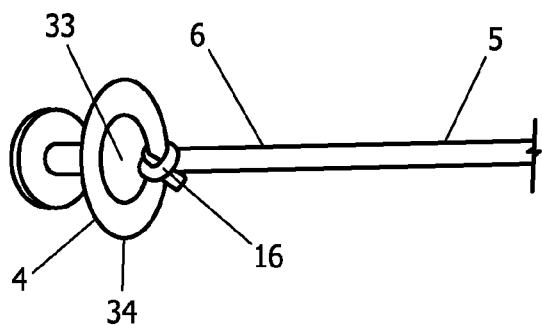
FIGS. 5A to 5C illustrate a variety of end treatments for the proximal end of elastic resistance lines along with complementary embodiment anchors on the panel of the present invention apparatus.
Figure 5B:
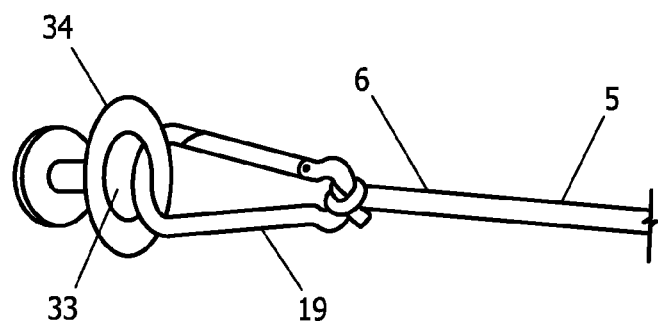
Figure 5C:
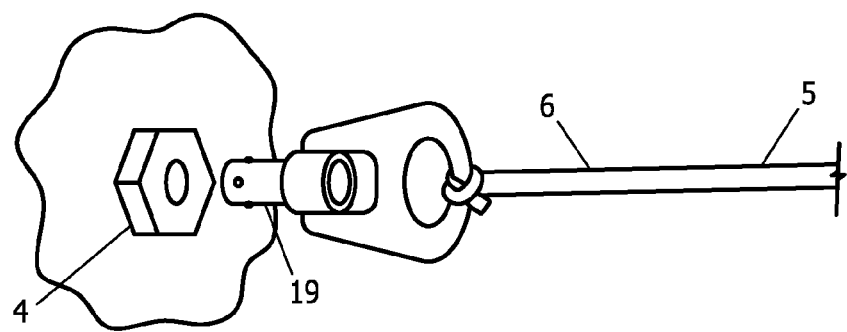
Figure 6A:
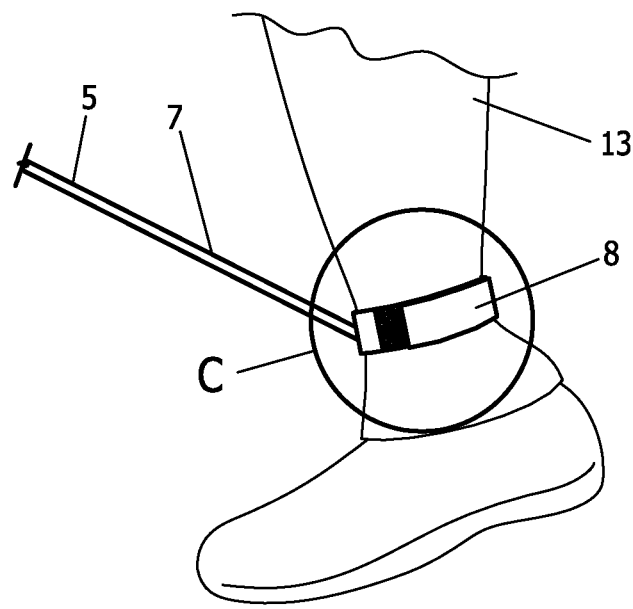
FIG. 6A illustrates the distal end of an embodiment resistance line with a permanently attached cinching mechanism that is secured to a lower limb. The detail image shows the cinching mechanism in an open state.
Figure 6A:
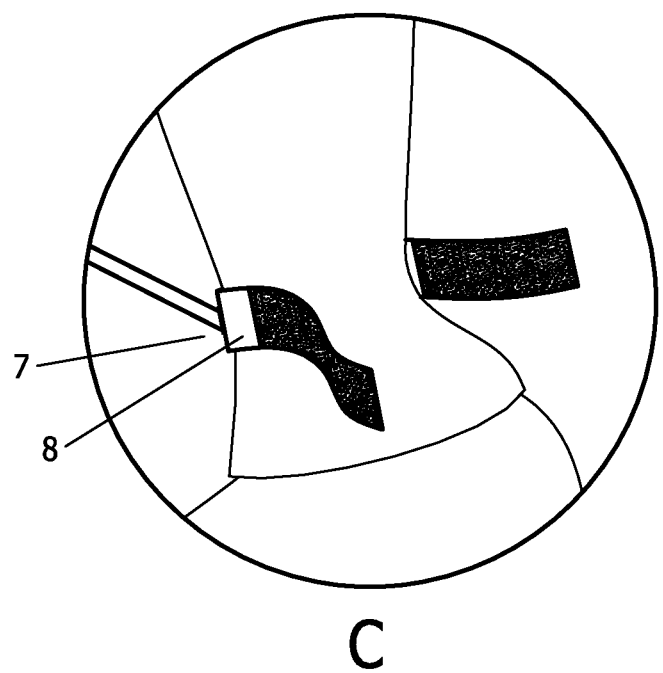
Figure 6B:
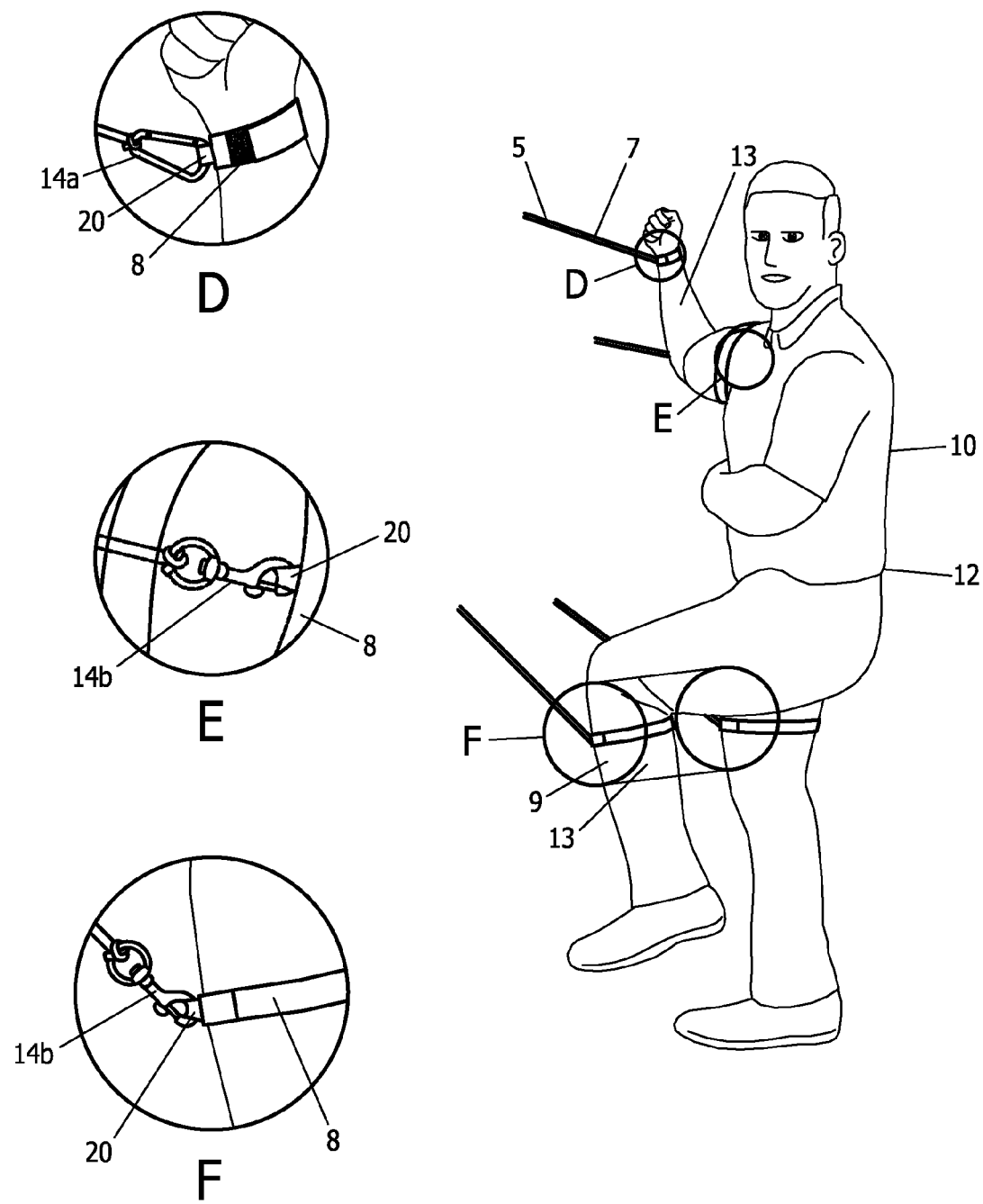
FIG. 6B illustrates embodiment resistance lines attached to a user, the detail images depicting a variety of end treatments for embodiment resistance lines in which the distal end includes a connector that may removably connect to a cinching mechanism worn by the user.
Figure 14:
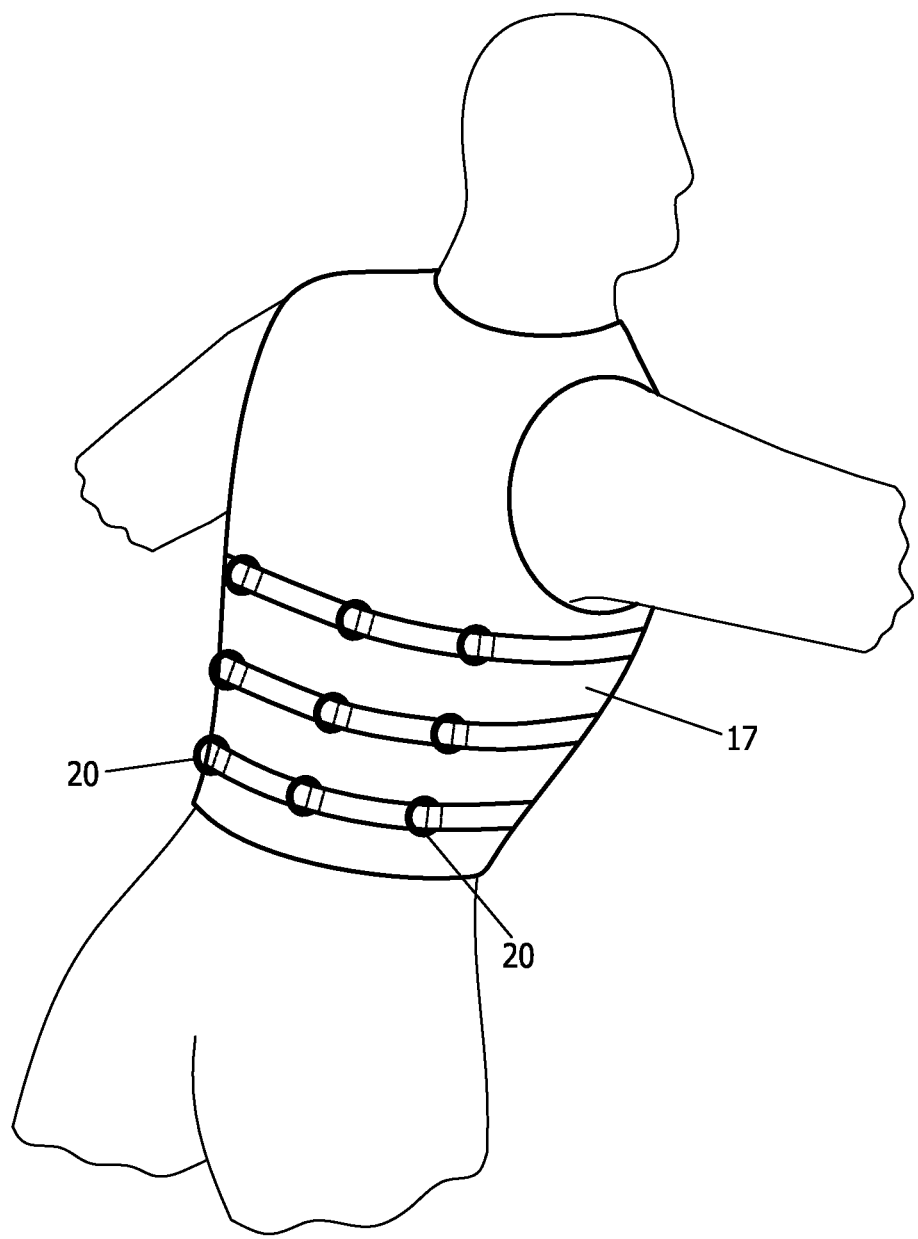
FIG. 14 shows an exemplary harness wearable by the user and which the discussed systems may comprise.

Each elastic resistance line 5 has a proximal end 6 and a distal end 7. Preferred embodiments of end treatments for resistance lines 5 are shown in FIGS. 5A to 5C and FIGS. 6A to 6B. As shown in those figures, distal end 7 of each elastic resistance line 5 is adapted to removably connect to one or more locations on the user's body. In a particular embodiment of this adaptation shown in FIG. 6A, distal end 7 includes a permanently attached cinching mechanism (e.g., a cuff) 8 that removably connects to one or more locations 9 on the user's body 10. As is discussed below and shown in FIG. 6B, distal end 7 of resistance line 5 may employ a mechanical connector that can removably attach to a cinching mechanism 8 worn by the user. An exemplary cinching mechanism 8 could be a hook and loop (Velcro) closable cuff as is shown in FIG. 6A. Other types of cinching mechanisms such as a belt or sizeable loop could be used. In the embodiment shown in FIG. 6A, cinching mechanism 8 can be permanently affixed to resistance line 5 and can directly embrace the trunk 12 or limbs 13 of the user. Alternatively in other embodiments, as are shown in FIG. 6B, distal end 7 is adapted to indirectly connect to one or more locations of the user's body. In this embodiment, distal end 7 includes a distal end connector 14 that can removably connect to a resistance line receiver 20 (for example, a ring or loop) on stand-alone cinching mechanism 8 or on harness 60. Detail images D, E and F in FIG. 6B show close-up images of how a connector 14 could indirectly connect to a cinching mechanism. An embodiment harness 17 is shown in FIG. 14. As shown in FIG. 6B, distal end connector 14 can be any type of known removable mechanical connector, including but not limited to such known connectors as a carabiner 14*a* (detail image D) or snap hook 14*b* (detail images E and F) that can attach to receiver 20.

Proximal end 6 of each elastic resistance line 5 is adapted for complementary attachment to one or more anchors 4 on panel 2. Hence, proximal end 6 is adapted to removably connect in mechanical fashion to one or more of the plurality of anchors 4. Likewise, each anchor 4 is shaped to receive (connect to) proximal end 6 of an elastic resistance line 5. Thus, the shape and mechanical function of each anchor 4 will depend upon the type of anchor connector 16, 19 desired for proximal end 6 of the resistance line 5 which will attach to it. As shown in the figures, a variety of differing end treatments for a resistance line 5 may be used.

For example, in a simple arrangement in which ribbon-like elastic bands are used, proximal end 6 of resistance line 5 can be left untreated so that it may be tied to anchor 4 via a knot 16. In such case, as is shown in FIG. 5A, a preferred anchor 4 could be an eye screw (a/k/a eye hook) 34. Instead of an eye screw, a mountable D-ring hanger may be used. Preferably, as is shown in FIG. 5B, when projecting anchors like eye screws or D-rings are used, the proximal end 6 of a resistance line 5 may include a mechanical anchor connector 19 such as, but not limited to the types of devices used for distal end connector 14 described above. Anchors 4 may be inset in panel 2 such that panel 2 has a more planar finish. This more preferred embodiment anchor 4 is shown in FIG. 5C. As shown in FIG. 5C, anchor 4 may be a female receptacle ("hole") that receives complementary male anchor connector 19 on the proximal end 6 of the resistance line 5. As shown in FIG. 5C, a preferred complementary embodiment male anchor connector 19 is a Kwik-Lok® lifting pin manufactured by Jergens, Inc. that is frictionally received by a female anchor 4 that comprises a Kwik-Lok® pin receptacle that screws into or secures onto panel 2.

Figure 7:
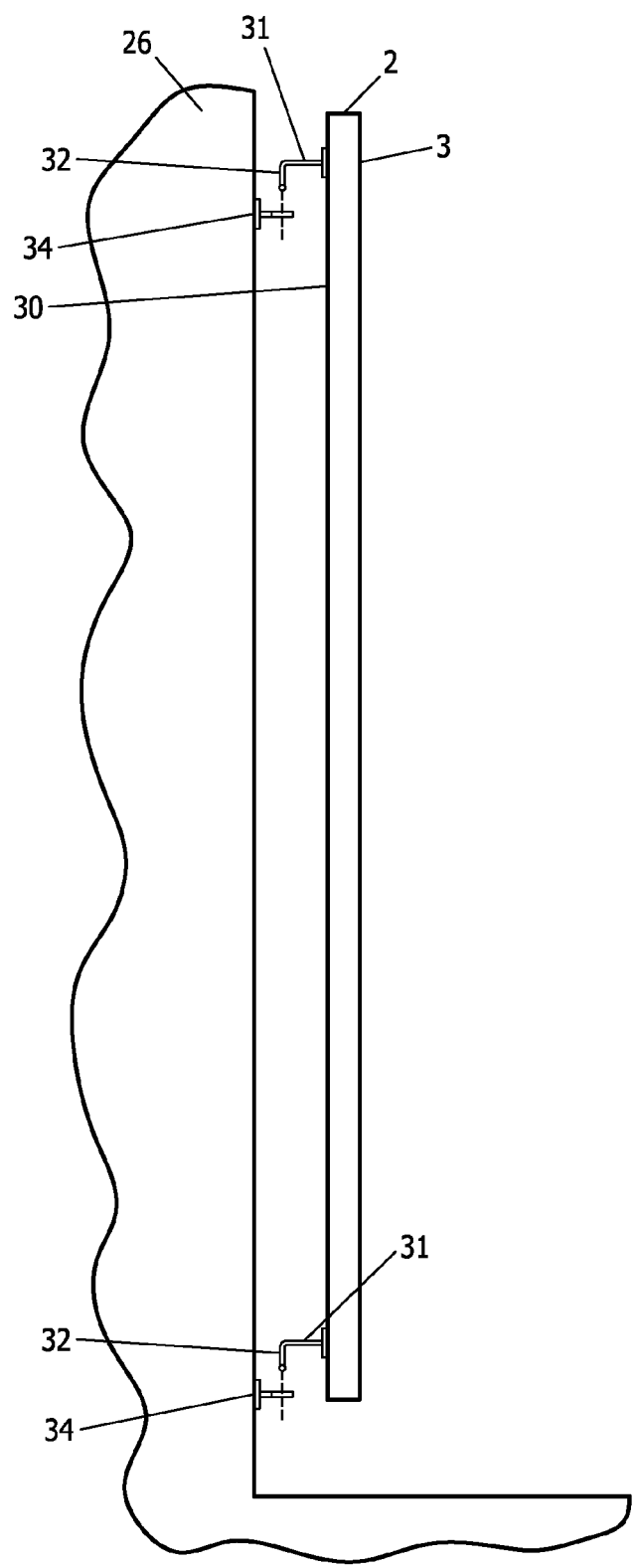
FIG. 7 shows an alternate embodiment panel mounting method for removably mounting the panel to a wall or frame.
Figure 8A:
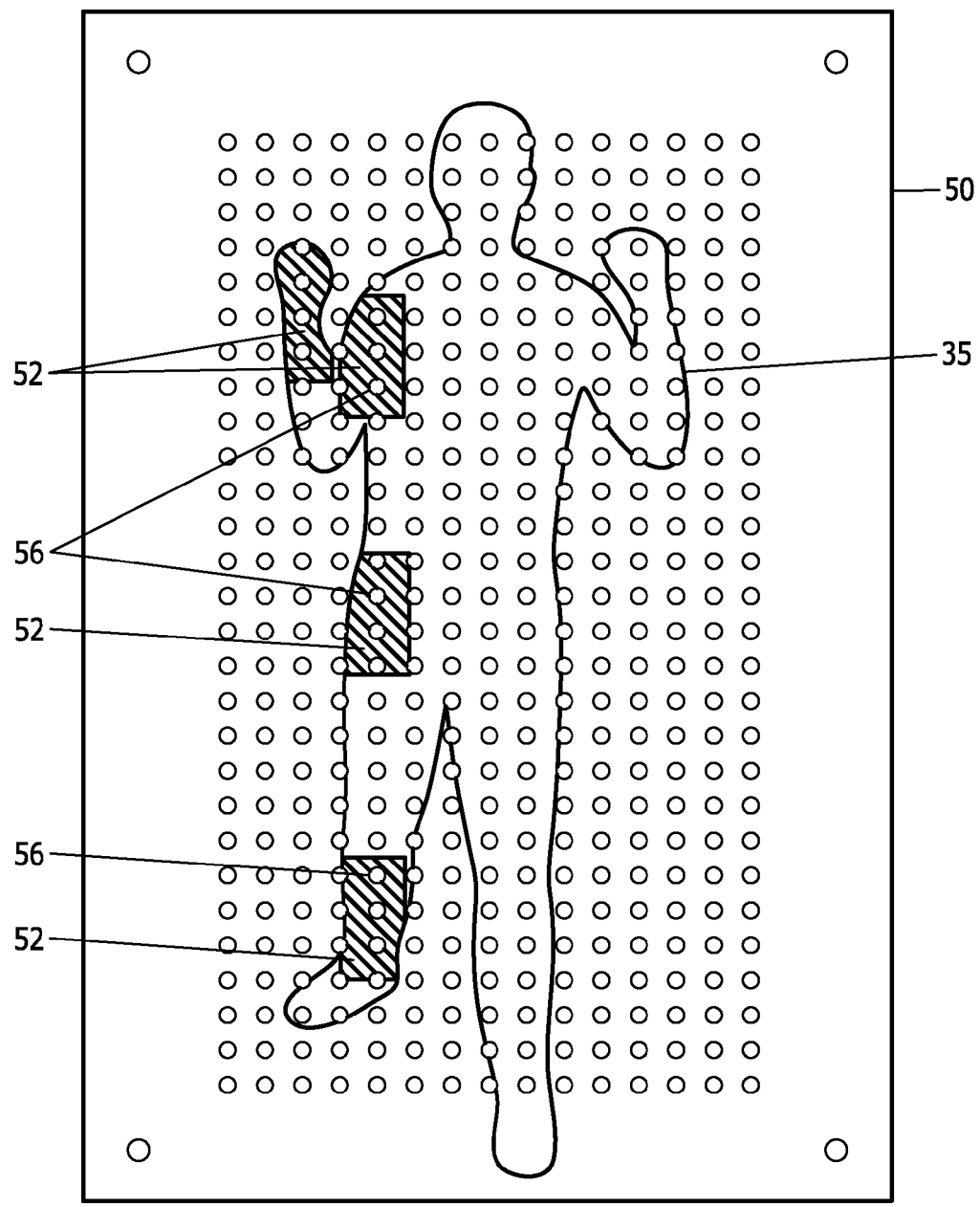
FIGS. 8A-8D shows printed images that depict human form images in body positions for striking, throwing, bat-swinging and ball-kicking.
Figure 8B:
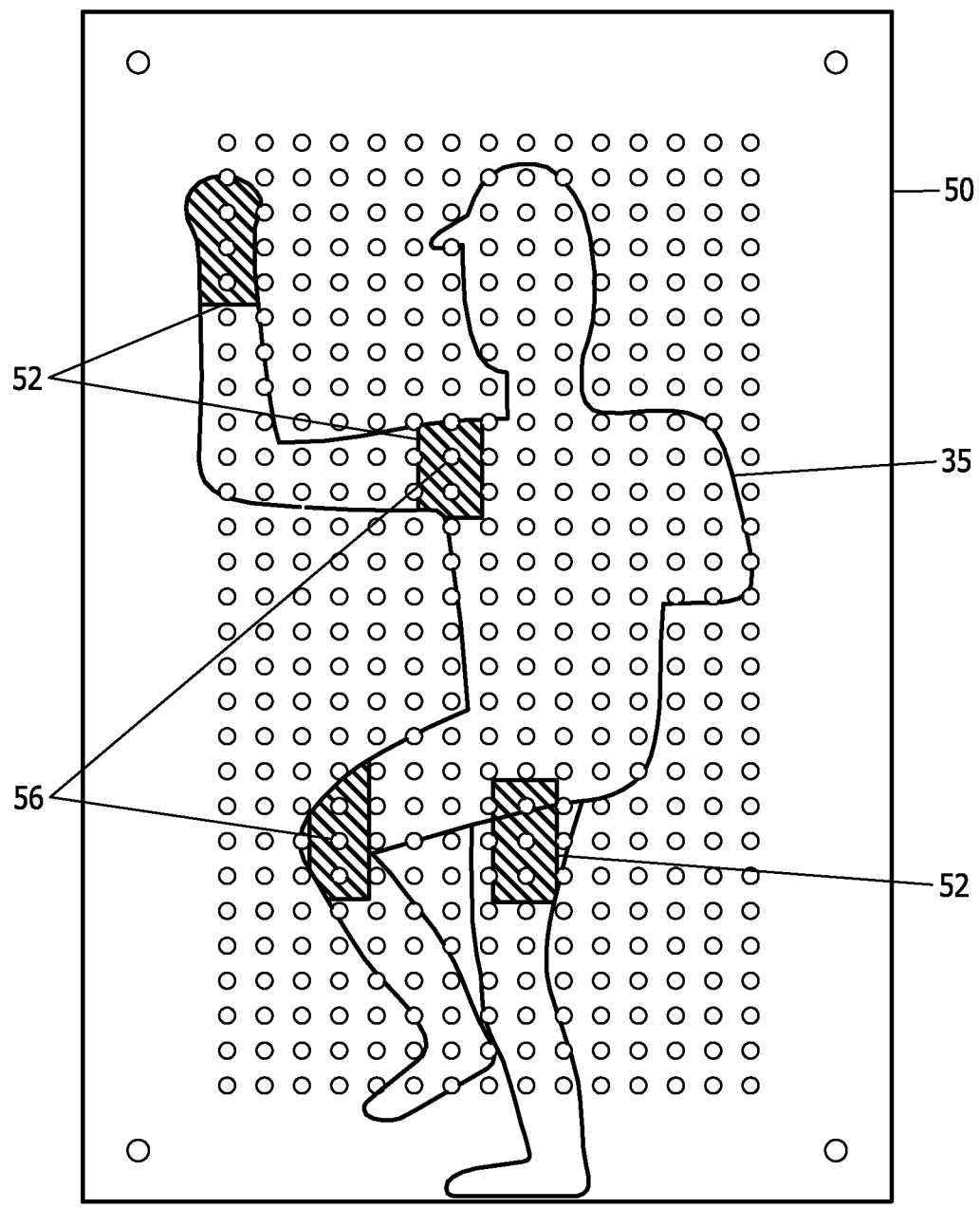
Figure 8C:
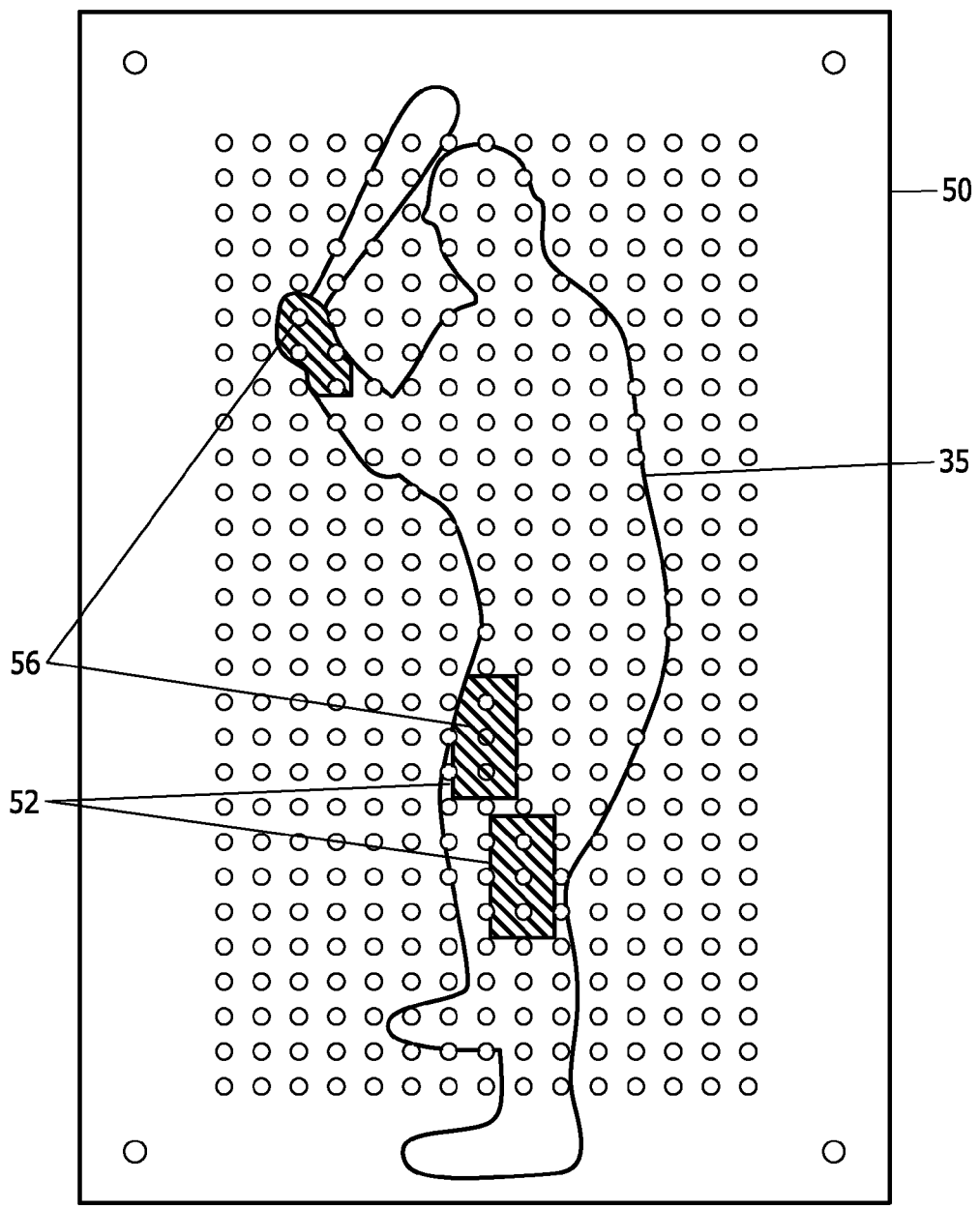
Figure 8D:
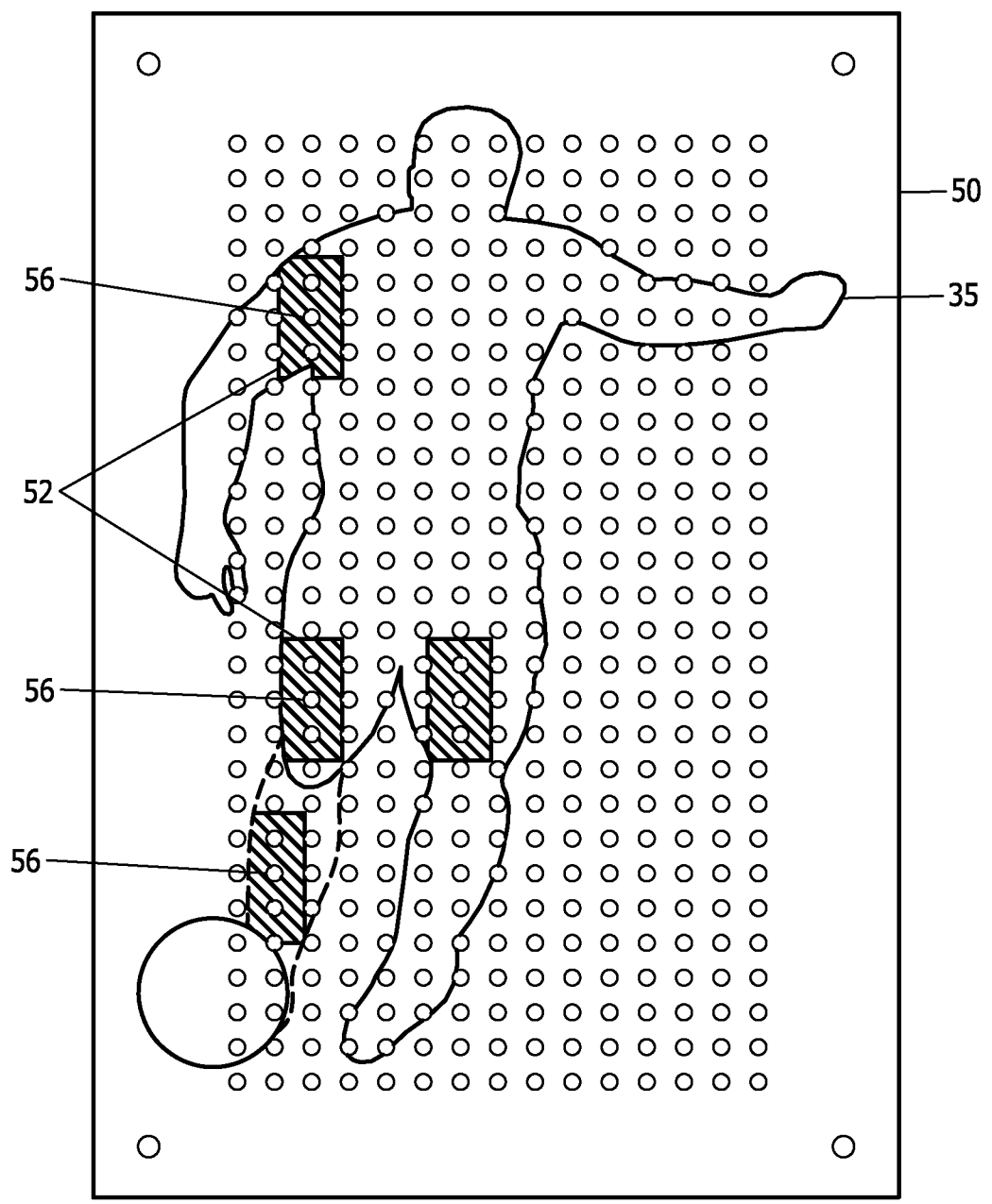

Panel 2 is preferably adapted as is described above for mounting on a wall 26, a frame 45 or both a wall 26 and frame 45. FIG. 7 shows panel 2 adapted for removable mounting to a wall. In this respect and as shown in FIG. 7, panel 2 includes one or more mechanical fastener elements 31 (in the form of preferred embodiment square bend screw hooks with downwardly depending elements 32 on back surface 30 of panel 2) that engage complementary fastener elements 34 (in the form of preferred embodiment eye hooks) on wall 26 to allow panel 2 to be removably secured, directly or indirectly, to a wall 26. As used herein the phrase "removably secured" means to securely fix in a manner that allows for non-destructive detachment. Any type of known mechanical attachment mechanism may be used to adapt panel 2 to be removably secured to a wall 26. The example is not meant to be limiting as to the type of wall-mounting adaptations or mechanical fastener elements that system 1 may include.

Figure 2:
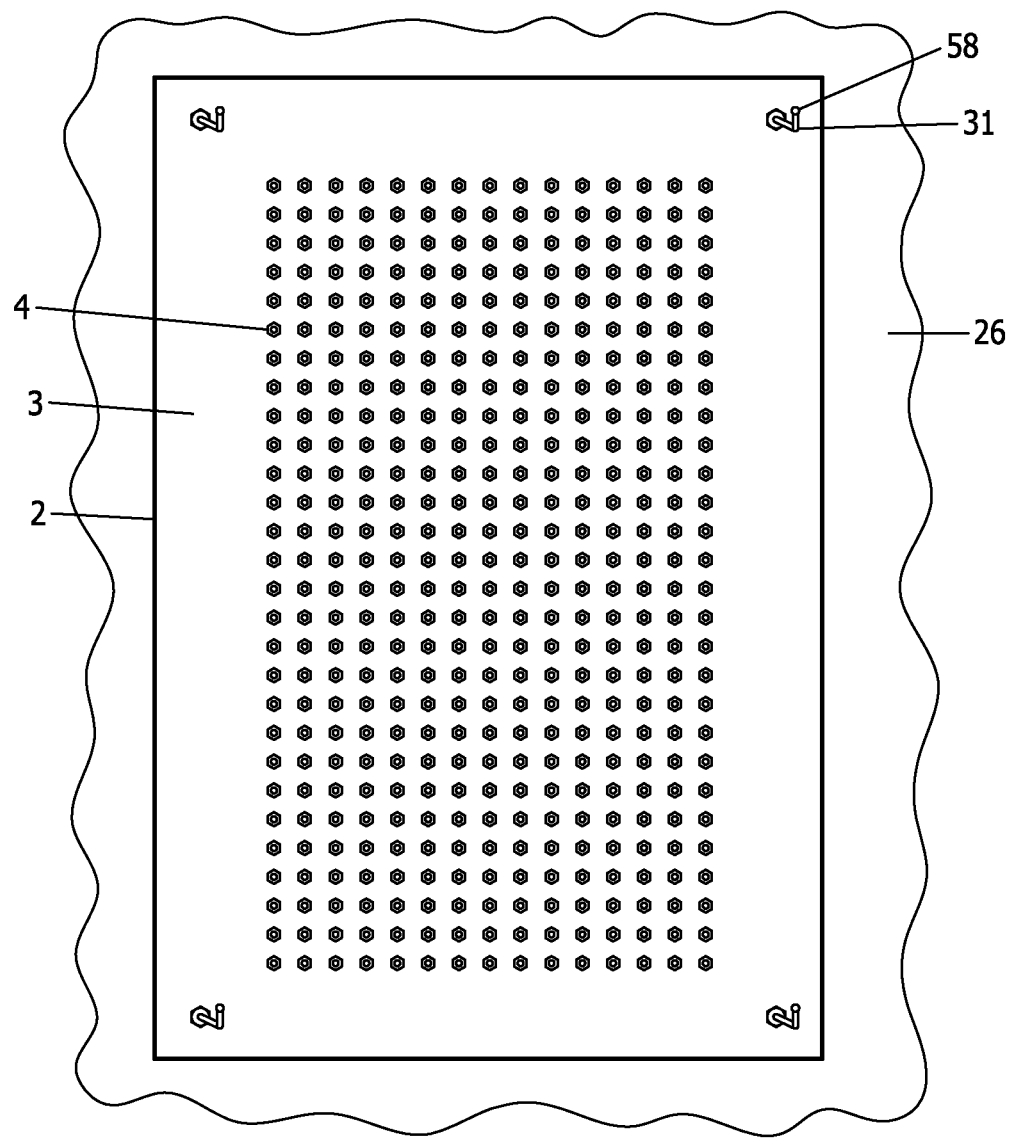
FIG. 2 is an elevation view of a preferred embodiment panel for use with the systems depicted in FIG. 1 and FIG. 9.

As shown in FIGS. 1-2, printer 61 of first embodiment system 1 is configured and sized to print a large sheet 50. Large sheet 50 is preferably pre-formed to include a pattern of access holes 56 matching the pattern of anchors 4 on panel 2. Alternatively, sheet 50 may be pre-formed with a pattern of weakened (via scoring or skip-cutting) aperture outlines. The areas of the sheet within the weakened aperture outlines (preferably circular) constitute "pop-out sections." These pop-out sections may be removed by hand from the sheet (typically after printing) to form access holes. The holes are formed by application of finger pressure applied upon the areas of the sheet within the aperture outline. Printer 61 is in electronic communication with computer 60. Computer 60 is programmed to receive input of a user's dimensional information along with a sport's specific movement to be trained. Computer 60, using that programming and input, determines a grouping 51 of anchors 4 to which each resistance line 5 attached to the user should connect while the user is engaged in the sport-specific body movement. Once the determination of anchor groupings is made the trainer or user can instruct computer 60 to send a "print" command to printer 61 to print a large sheet for 50 overlaying on panel 2. Thus, upon input of such information into computer 60, computer 60 can be instructed to send a print command to printer 61 to print large sheet 50. Printed sheet 50 can have either or both of printed verbal or graphic instruction as to where to attach resistance lines 5. Upon receiving such command, printer 61 prints large sheet 50.

Figure 3A:
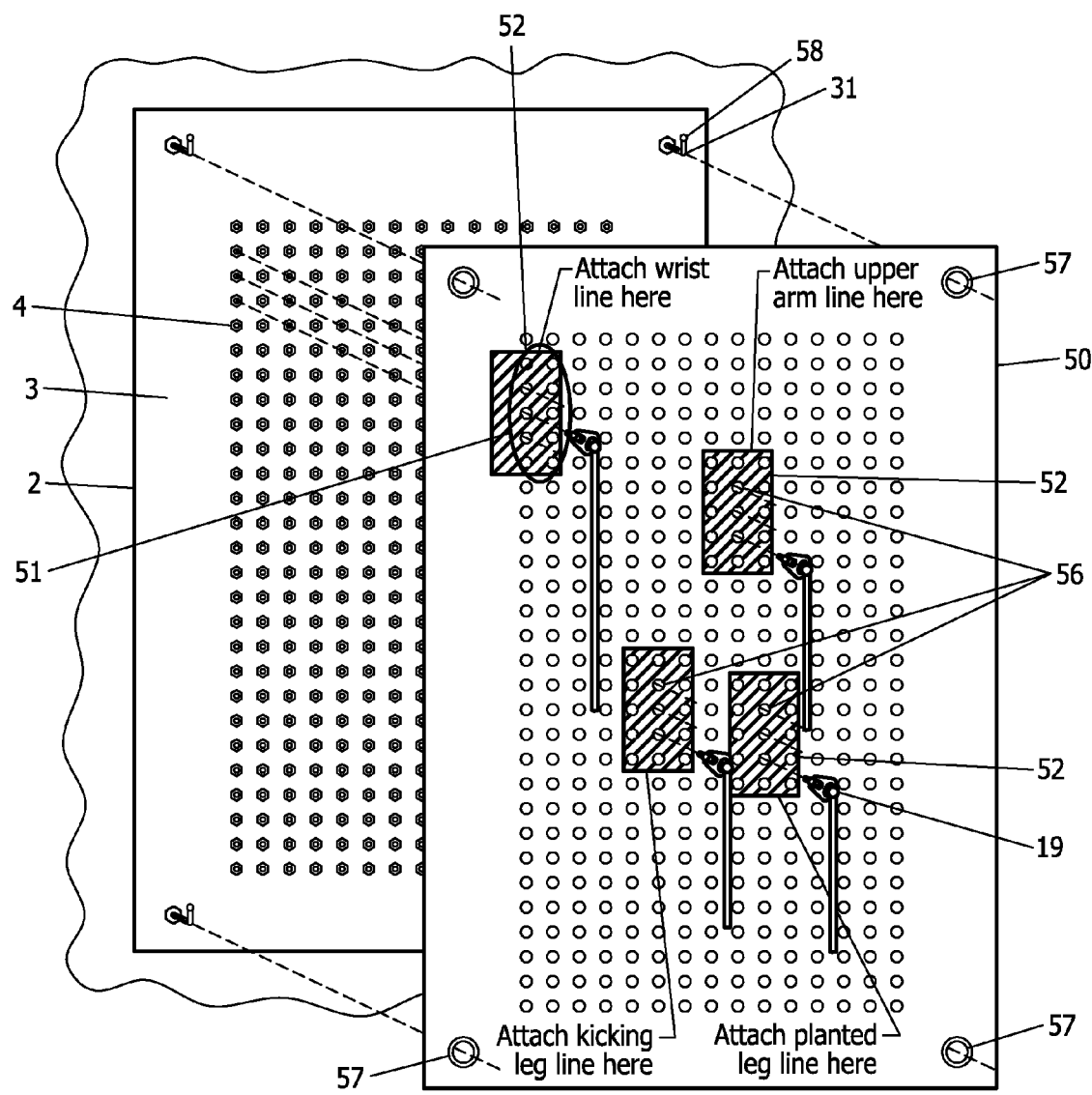
FIG. 3A is a perspective view of a sheet intended for use with the embodiment system shown in FIG. 1 being overlaid upon the embodiment panel of FIG. 2, the sheet having printing that demarcates anchor groupings that should receive the resistance lines to train the subject movement for the particular user and instructing the user where to attach resistance lines.

As shown in FIG. 3A, printed sheet 50 includes one or more demarcated areas 52. Each demarcated area 52 is located on sheet 50 and demarcates an anchor grouping 51 among the plurality anchors 4 on panel 2 when sheet 50 is in the overlaid position on the panel. Sheet 50 also identifies a location on the user's body at which distal end 7 of a resistance line 5 should connect. An embodiment sheet 50 is depicted in FIG. 3A. Sheet 50 is adapted to overlay and removably attach to front surface 3 of panel 2. Sheet 50 while in the overlaid position on the panel allows access to the computed anchor groupings 51 among the plurality anchors through sheet 50 so as to allow each anchor in each anchor grouping 51 to connect to a resistance line. As disclosed in this figure, sheet 50 contains indication (e.g., such as through printing on the sheet) of the optimal locations for connecting resistance lines to the user and the panel for the particular sport-specific movement being trained based by that particular user. In FIG. 3A the indication is textual (i.e., verbal).

Figure 3B:
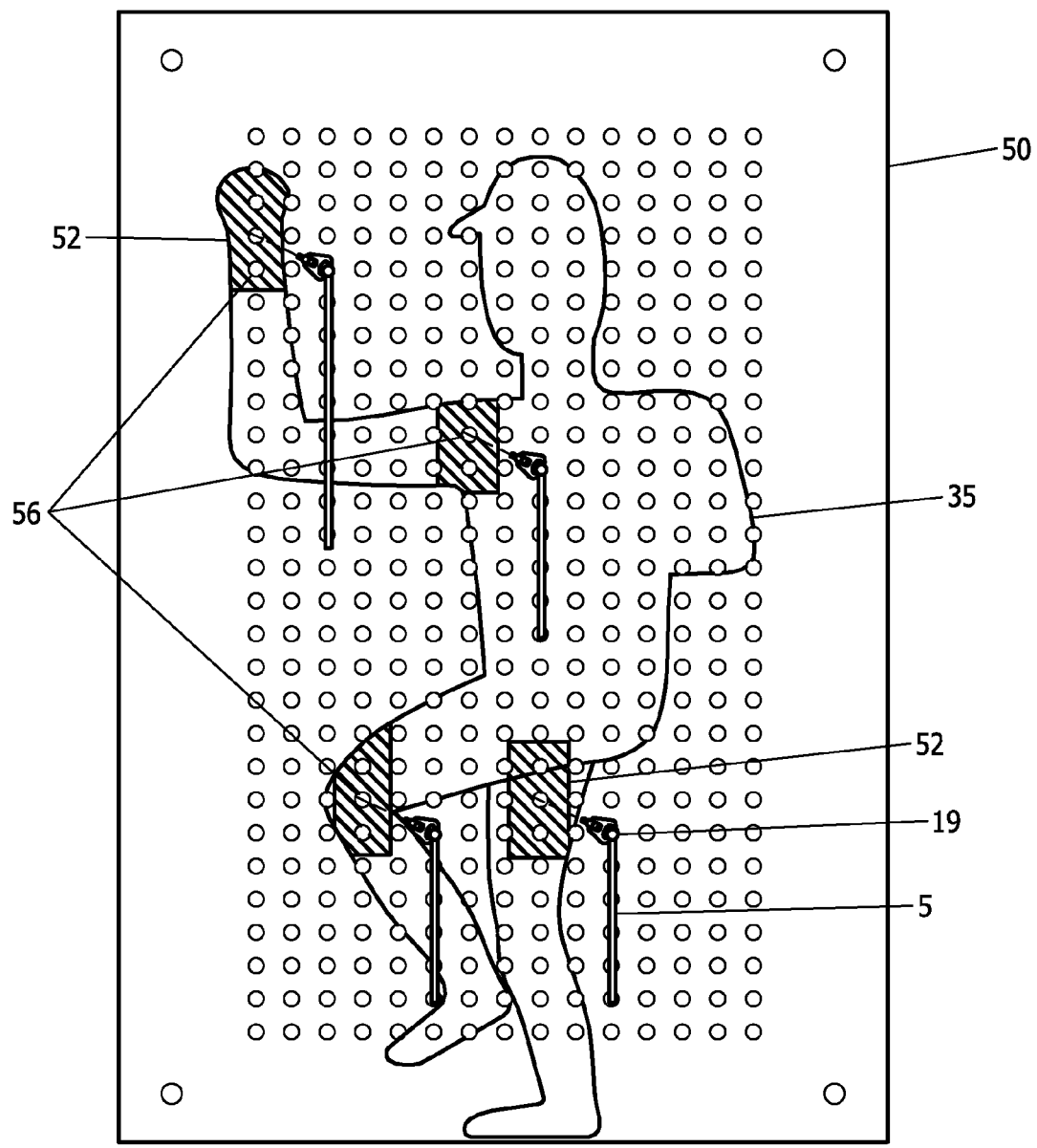
FIG. 3B is an elevation view of a more preferred embodiment sheet intended for use with the embodiment system of FIG. 1 and panel of FIG. 2 graphically showing: a) the size-specific silhouette of a human body in a sport-specific movement; b) the demarcated groupings of anchors that should receive the resistance lines to train the subject movement for the particular user and c) where on the body a resistance line emanating from a particular demarcated grouping should attach.

As is shown in FIG. 3B, a more preferable first embodiment system includes the feature that sheet 50 depicts a human form image 35. Human form image 35 defines an area that contains the one or more demarcated areas 52. Each demarcated area 52 located on the sheet defines an anchor grouping 51 among the plurality anchors 4 on panel 2 when sheet 50 is in the overlaid position on the panel. Sheet 50 is adapted to overlay and removably attach to front surface 3 of panel 2. Sheet 50 while in the overlaid position on the panel allows access to the anchor groupings 51 among the plurality anchors through sheet 50 so as to allow each anchor in each anchor grouping 51 to connect to a resistance line. As noted, human form image 35 has one or more demarcated areas 52. When overlaid on panel 2, each demarcated area 52 defines an area located on panel 2 that represents an optimum resistance origin point for optimally training a user of certain dimensions. In this respect, each sheet 50 has demarcated areas that, when sheet 50 is overlaid on panel 2, each define an anchor grouping 51 on the panel. Each anchor grouping 51 may include one or more anchors 4. Each demarcated area 52 also graphically identifies a location 9 on the user's body 10 at which distal end 7 of a resistance line 5 should connect, and a location on panel 2 at which proximal end 6 of the same resistance line 5 should connect, while the user 10 is engaged in the sport-specific movement. For optimum, safe training, the user should connect the resistance line to any of the anchors within the anchor grouping defined by a demarcated area.

Figure 4:
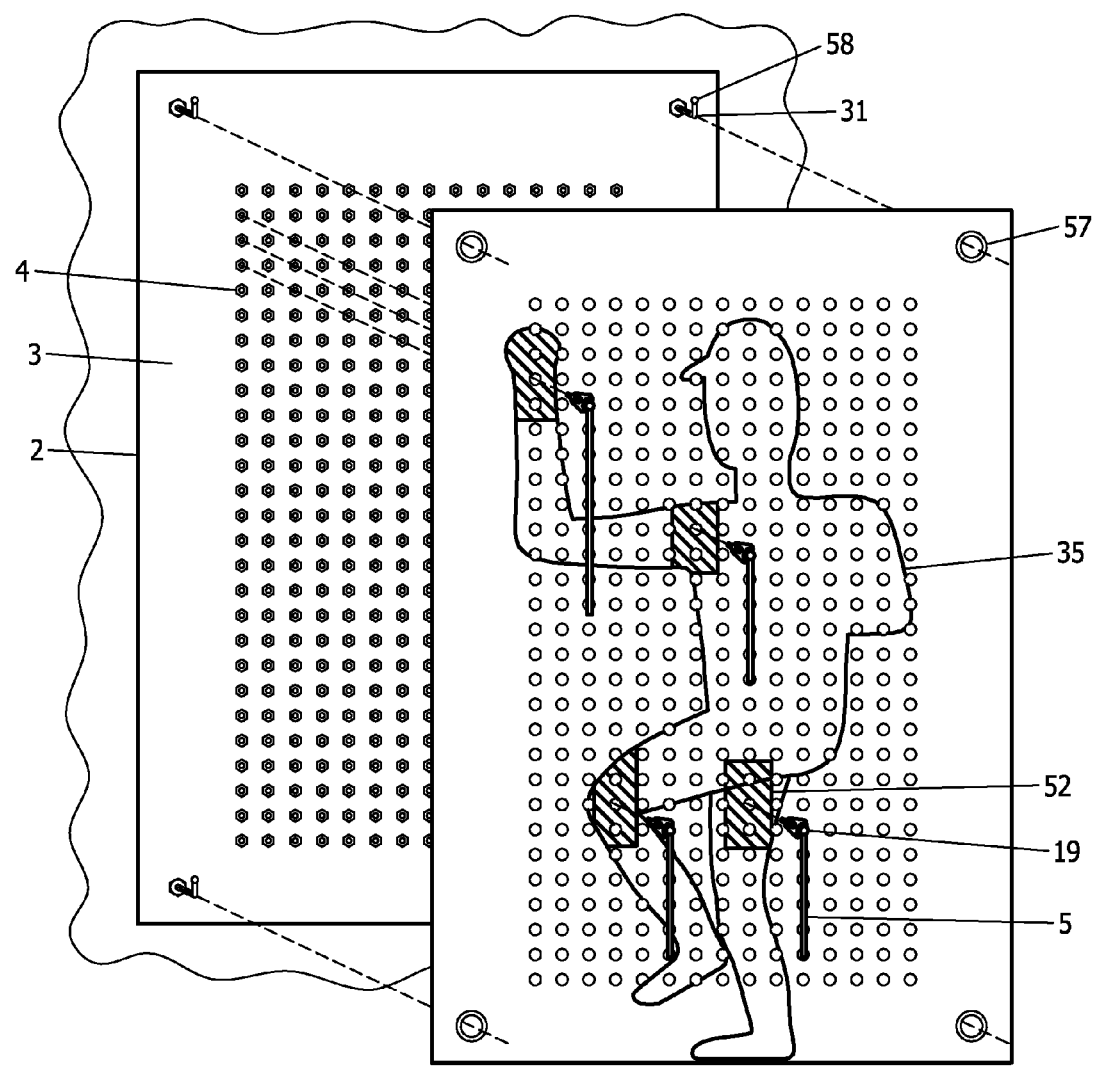
FIG. 4 is a perspective view showing the sheet of FIG. 3B being overlaid and received by the panel of the embodiment system depicted in FIG. 1.

As noted, printed sheet 50 is adapted to overlay and removably attach to front surface 3 of panel 2. In an example adaptation shown in FIG. 4, sheet 50 includes mounting holes 57 that can be received by square bend screw hook 31 with upwardly depending element 58. In FIG. 4, mounting holes 57 are grommetted for durability. Holes 57 can be grommetted after printing. Each demarcated area 52 of sheet 50 includes anchor access holes 56. Anchor access holes 56 allow access to each anchor 4 in groupings 51 through sheet 50, when sheet 50 is in the overlaid position on panel 2. Through this access, each anchor 4 in a grouping 51 can connect to a resistance line 5 through sheet 50. It is preferable to use the complementary female anchor 4 and male connector 19 complementary connectors of FIG. 5C to reduce the number of needed holes 56 in sheet 50 to access anchor groupings 51. If projecting anchors 4 are used such as are shown in FIGS. 5A and 5B, then for sheet 50 to properly overlay panel 2 in a flat arrangement, sheet 50 will need to include a pattern of holes 56 to fully match the entire pattern of anchors 4 on panel 2. If female anchors are used, then sheet 50 can be either the fully perforated sheet depicted in the drawings or the above-described sheets in which holes can be limitedly formed within the demarcated areas as needed after printing from the weakened aperture outlines (in the demarcated areas) to access the anchors underneath the printed demarcated groupings 51 on sheet 50.

As shown in FIG. 3B, human form image 35 on panel 2 also depicts a body position to be assumed by the user to begin using the apparatus to train a particular body movement. By virtue of this graphic instruction, the user knows for each resistance line: a) where on his or her body to secure the resistance line; b) where on the panel to secure that same resistance line; and c) the position from which to begin the sport-specific resistance training. In the depicted system of FIG. 1 the sheet displays a human form image 35 of a pitcher in a "wind-up" position and denotes which anchors 4 should receive which resistance lines 5 to properly train the sport-specific movement.

Figure 9:
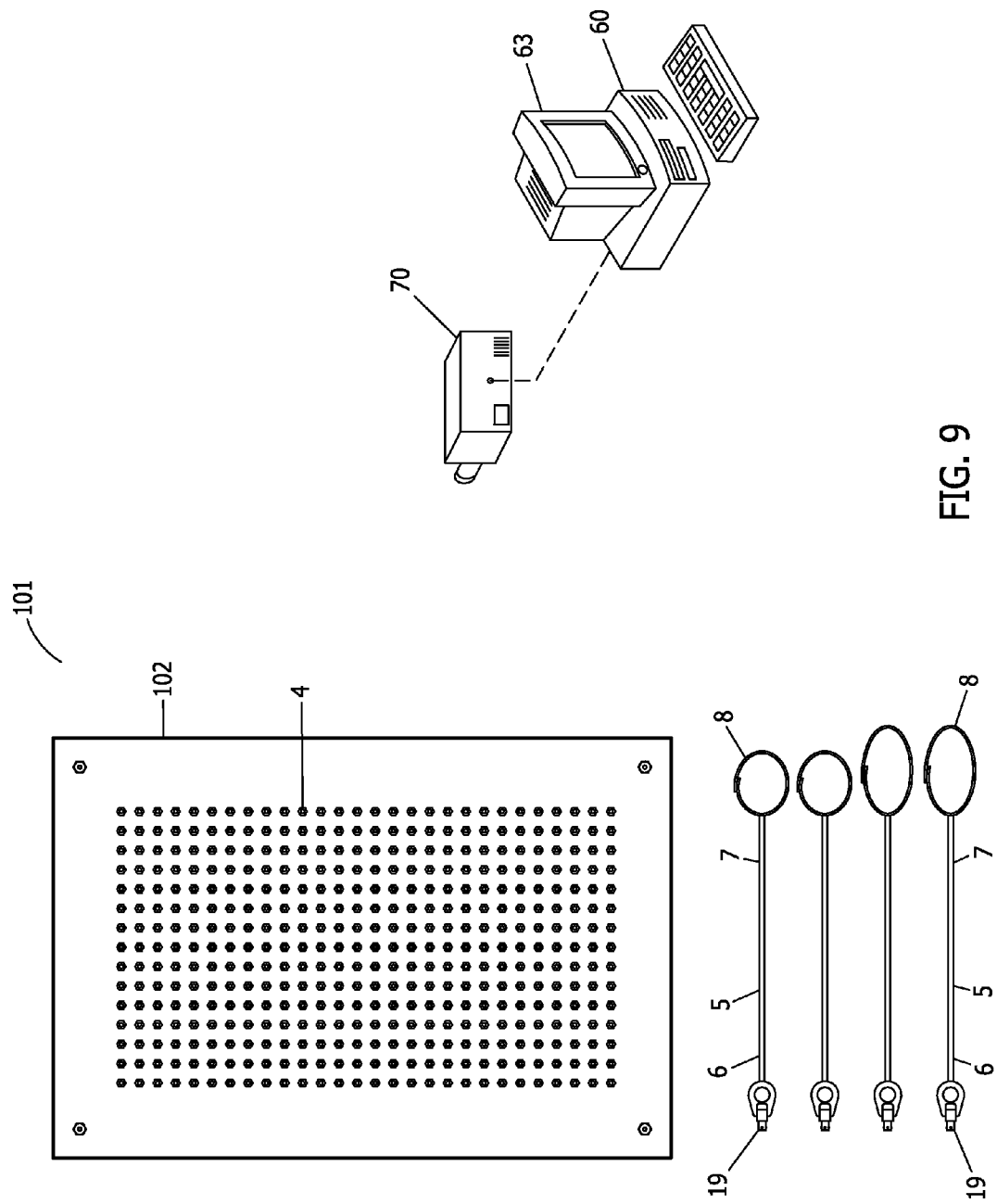
FIG. 9 is a schematic of a second embodiment system that includes a panel, plurality of resistance lines, computer and a projector.
Figure 10A:
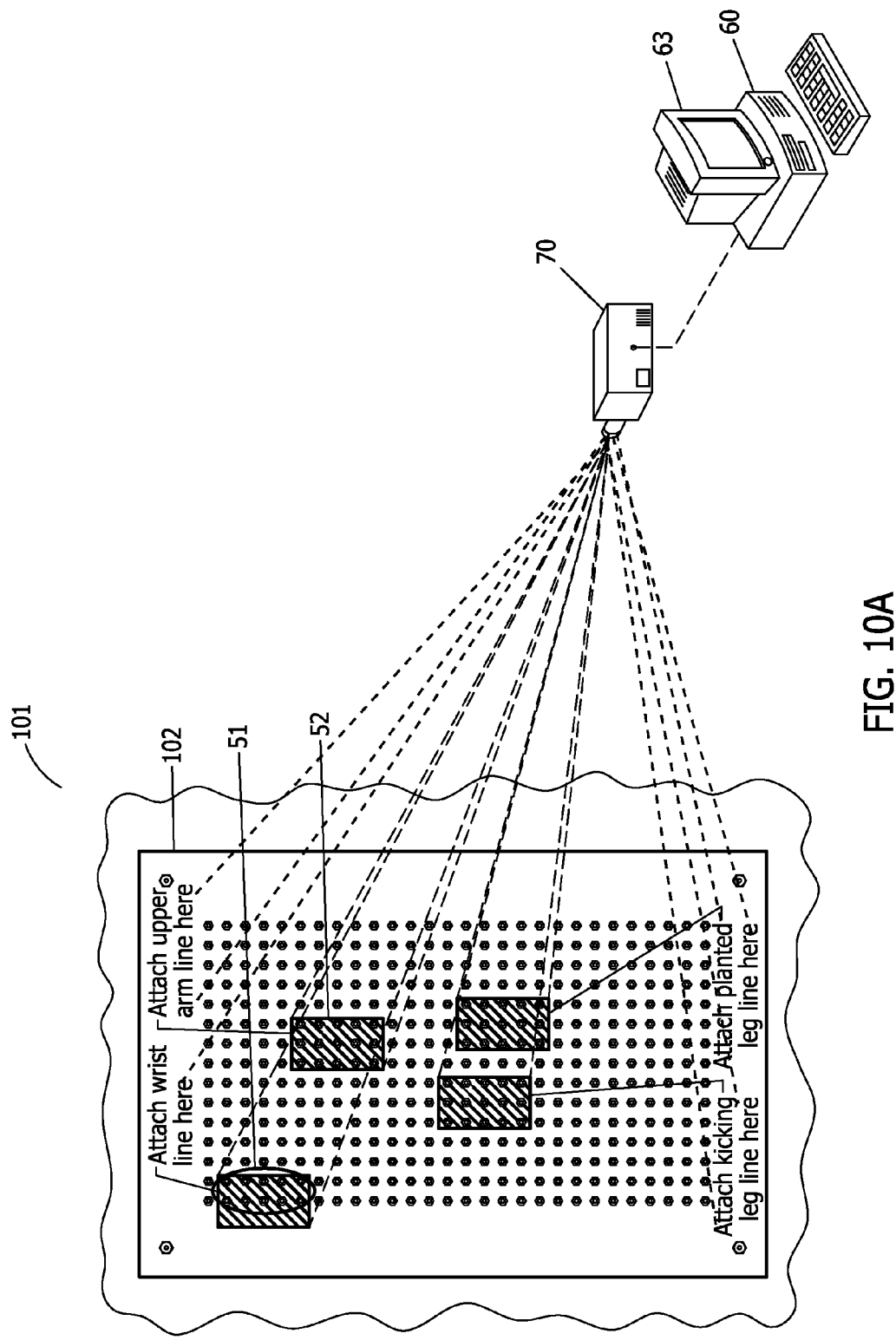
FIG. 10A is a view of a projected system display on a panel in accordance with the embodiment shown in FIG. 9, the projected display showing anchor groupings that should receive the resistance lines to train the subject movement for the particular user and instructing the user as the location of attachment of resistance lines on the user's body.
Figure 10B:
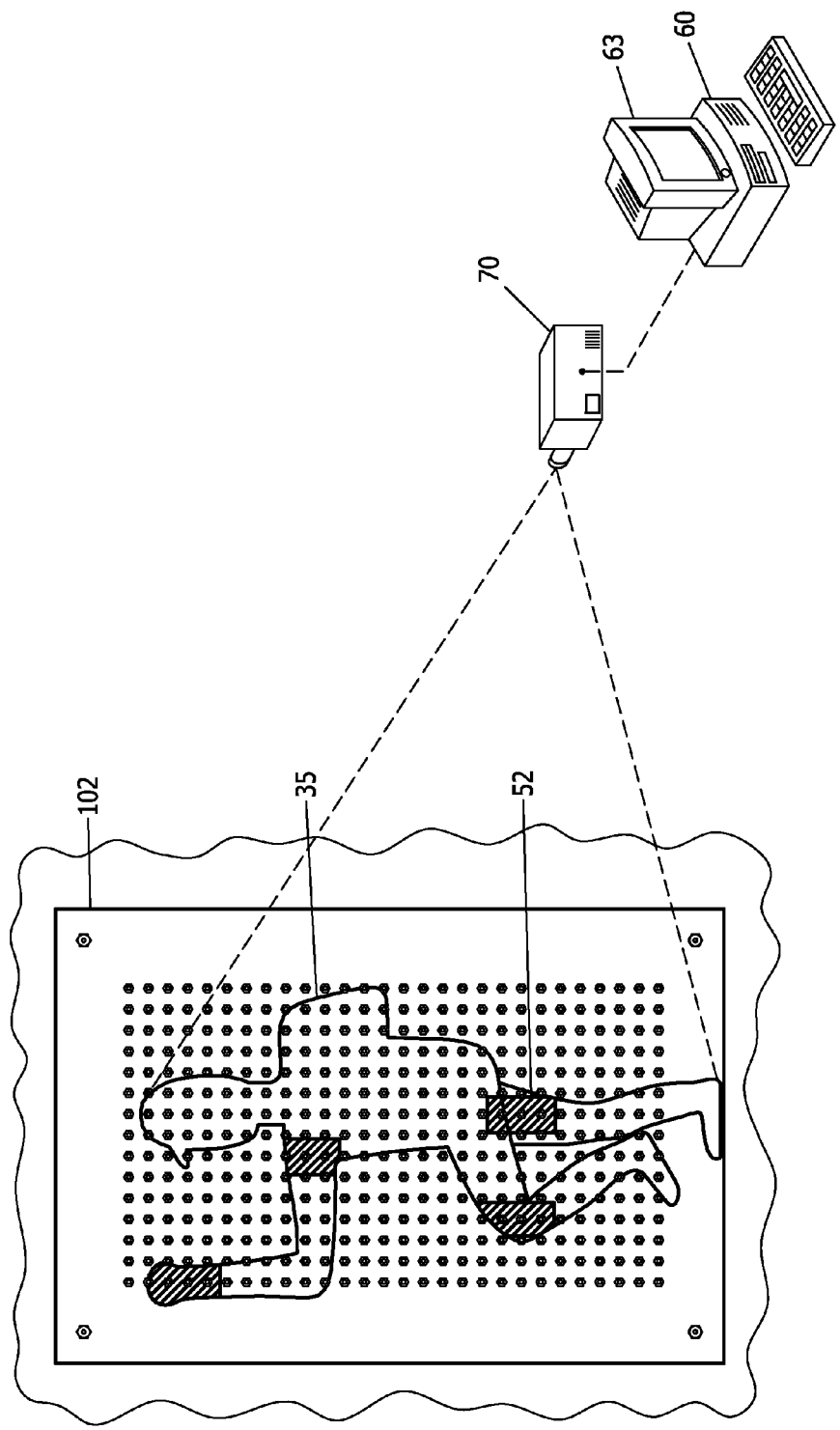
FIG. 10B is a view of a projected image on a panel in accordance with the embodiment shown in FIG. 9, the image showing: a) a size-specific human image figure performing a sport-specific movement; b) anchor groupings that should receive the resistance lines to train the subject movement for the particular user; and c) where on the body a resistance line emanating from a particular anchor grouping should attach.

In a second embodiment a kinetic chain training system 101 provides resistive force to a user's body while the user is engaged in a particular body movement. This embodiment system is shown in FIGS. 9, 10A and 10B. The second embodiment system comprises panel 102 having front surface 3 and a plurality of anchors 4 disposed in a pattern across front surface 3 of panel 102. The panels of the first and second embodiments are similar in construct. System 101 further includes the plurality of elastic resistance lines 5 described above with respect to the first embodiment system. This second embodiment system 101 includes computer 60 and projector 70 in electronic communication with computer 60. Computer 60 is programmed to receive input regarding, or is adapted to self-determine through positional sensors, the relative location of the projector vis a vis the panel. Once that relative location is established, which in the physical therapy setting is normally not disturbed after being established, the computer can receive input as to user-specific information. Computer 60 is also programmed to receive input as to a user's body dimensions 11 and the particular body movement being trained by the user. Using that input, computer 60 determines an anchor grouping 51 to which each resistance line 5 attached to user 10 should connect while user 10 is engaged in the particular body movement. After making that determination, computer 60 outputs a signal 62 to projector 70 instructing projector 70 to display on panel 102 an image with demarcated areas 52. Each demarcated area 52 indicates an anchor grouping 51 to which each resistance line 5 attached to user 10 should connect while user 10 is engaged in the sport-specific body movement.

Preferably, projector 70 will display a human form image 35 on panel 102. More preferably, human form image 35 also defines an area containing the one or more demarcated areas 52. Each demarcated area 52 defines an area on panel 102 in which is located an anchor grouping 51 on panel 102. Each demarcated area 52 also graphically identifies a location on the user's body 10 at which distal end 7 of a resistance line 5 connected to an anchor grouping 51 should attach while the user is engaged in a particular body movement. Preferably, displayed human form image 35 depicts a body position to be assumed by the user to begin using the apparatus to train the sport-specific movement.

More preferably, each projected image will also graphically depict a human form image in a position identifiable with the sport-specific movement being trained. The human form image would include demarcated areas 52 showing where on panel 102 resistance lines should be secured in order to train the particular kinetic chain movement. In a preferred embodiment, the computer will instruct the projector to project a display that indicates the sports movement to which it applies and the identity and dimensional information of the particular user.

In the example of a system utilized in a field goal kicking motion configuration, the projected display could be a human form image of a kicker in a "ready-to-strike-the-ball" position. The projected image might also include indications for the user where the resistance lines should be attached to the user's body.

Each projected display is generated based upon the input of a user's specific dimensional information. Thus, inputting dimensional information for a left-handed user having an exemplary height 5'5" would generate a different projected image than when inputting dimensional information for a right-handed user of an exemplary height of 6'11". Each projected display contains indication of the optimal locations for connecting resistance lines to the panel for the particular sport-specific movement being trained based by that particular user.

Figure 11:
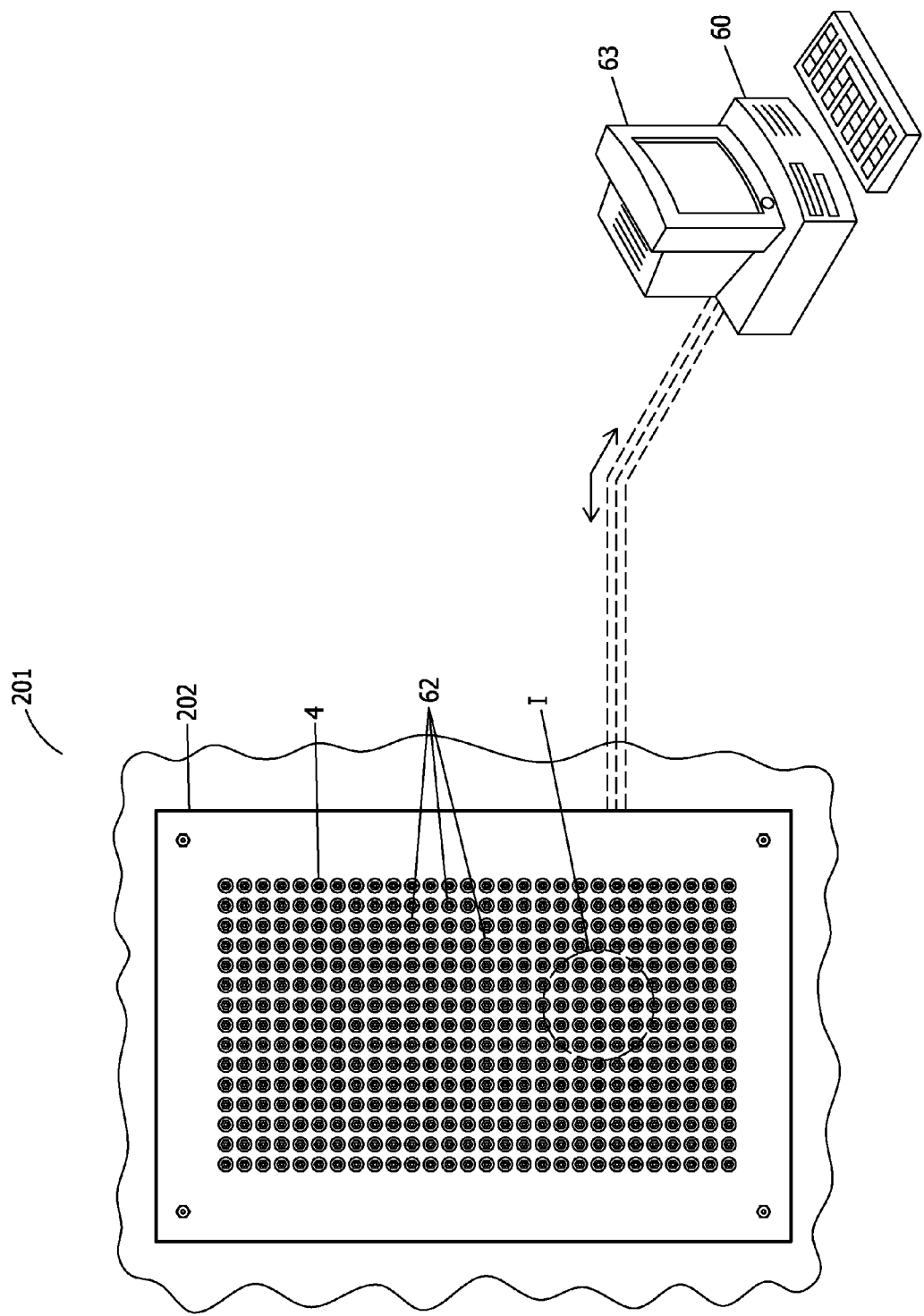
FIG. 11 is a schematic showing the implementation of a third embodiment system comprising an enhanced panel in electronic communication with a computer. The panel having anchors with integral or proximate indicators to indicate the anchors that should receive resistance lines to train a sport-specific movement for a particularly dimensioned user.
Figure 12:
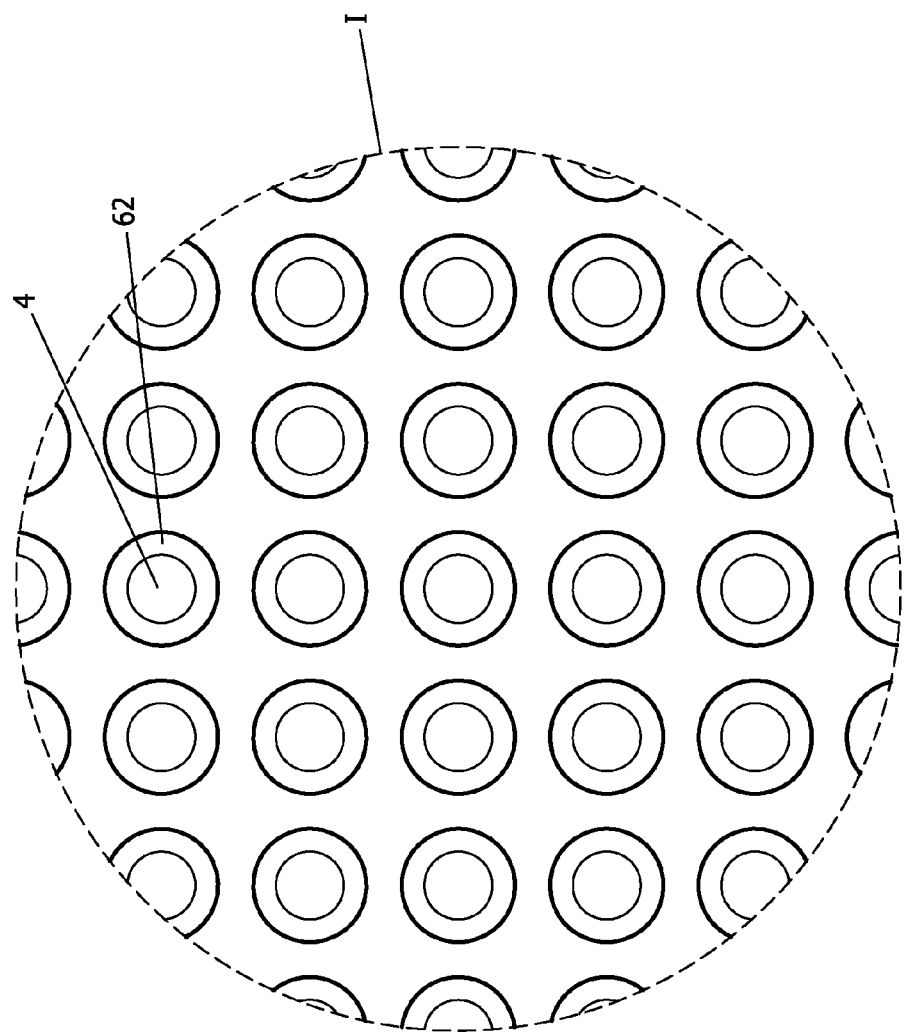
FIG. 12 is a detail view of a portion of the embodiment panel depicted in FIG. 11 and having electronically activated indicators that encircle the anchors, the indicators on the panel being in electronic communication with a computer.
Figure 13:
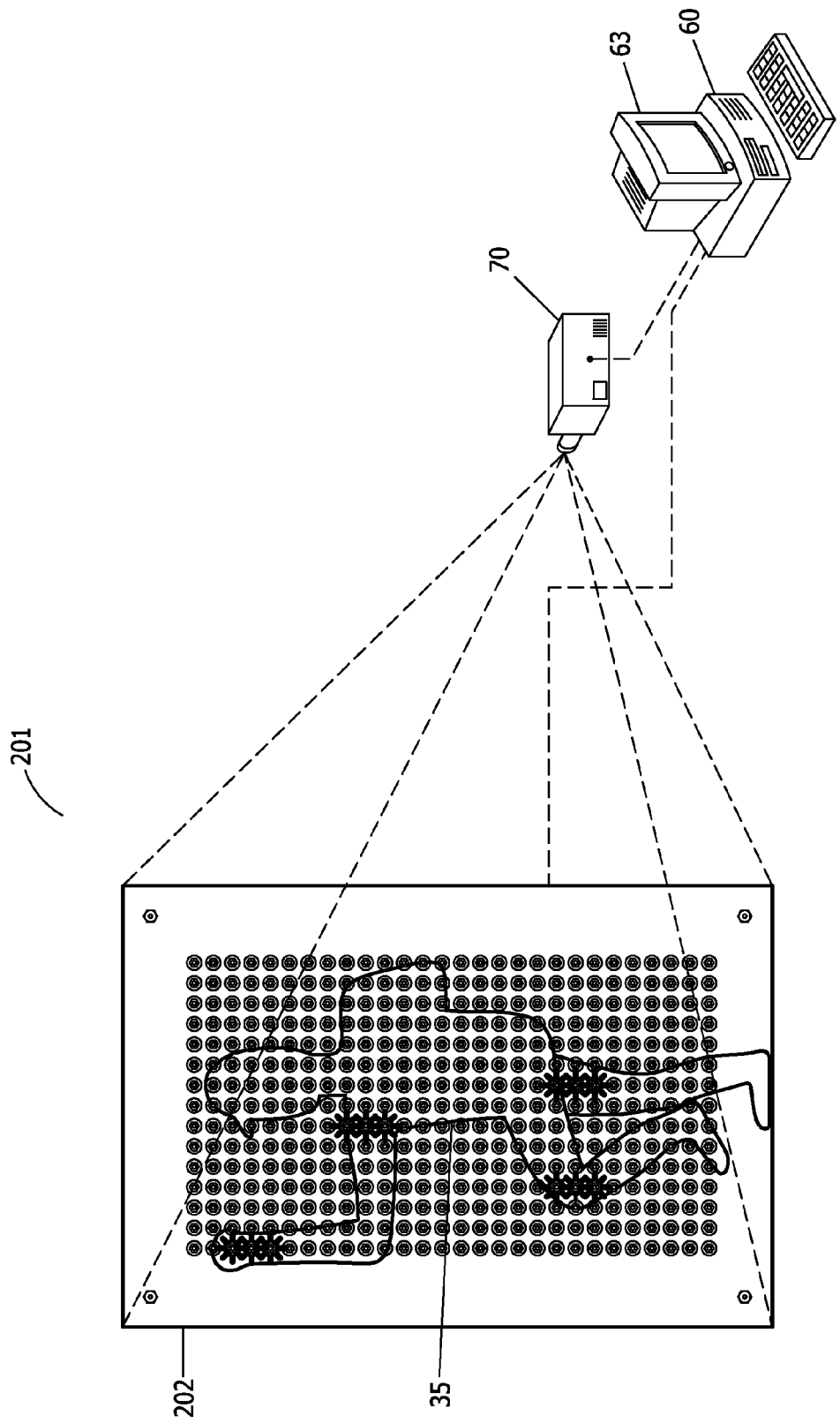
FIG. 13 is a schematic of the panel of the system shown in FIG. 11 having illuminated groupings of anchors and a projected image on the panel in accordance with an enhanced embodiment, the image showing: a) a size-specific human image figure performing a sport-specific movement; and b) where on the body a resistance line emanating from a particular anchor grouping should attach.

A third embodiment of the invention is shown in FIGS. 11 to 13. This embodiment discloses a kinetic chain training system 201 for providing resistive force to a user's body while the user 10 is engaged in a sport-specific body movement. System 201 comprises electrified panel 202, which is in wired or wireless electronic communication with computer 60. Panel 202 is similar to panels 2 and 102 of the first and second embodiment, in that it has front surface 3 and a plurality of anchors 4 disposed in a pattern across front surface 3 of panel 202. Panel 202 further includes an electronically activated indicator or signal 62 proximate to or integral with each of the plurality of anchors 4.

Indicators 62 could be of any type including, but not limited to light, verbal display, color change display, electromagnetic signal or other type of indicator. In the depicted embodiment, the indicator 62 is an illuminating ring encircling anchor 4. In response to the input into computer 60 of the user's dimensions and indication of what sport-specific activity is being trained, computer 60 outputs a signal to panel 202 instructing the panel to turn on the indicator 62 for the particular anchor groupings 51 that should receive the resistance lines 5. The third embodiment system also includes a display device 63 in communication with computer 60 that provides indication (as instructed by the computer) of where on the user's 10 body or harness 17 a resistance line 5 connected to a particular anchor grouping 51 should optimally be placed.

System 201 includes a plurality of elastic resistance lines 5 as described above. Computer 50 is programmed to receive input as to a user's body dimensions and the sport-specific body movement being trained and determine an anchor grouping 51 to which each resistance line 5 attached to user 10 should connect while user 10 is engaged in resistance training the sport-specific body movement. After making that determination, computer 60 outputs a signal 62 to certain indicators 62 on panel 202 instructing or triggering the activation of the indicators 62 for the anchors 4 in each anchor grouping 51 to which each resistance line 5 attached to user 10 should connect. FIG. 13 depicts the system with the indicators 62 illuminated, thereby instructing the user of the attachment points for resistance lines.

Display device 63 is in communication with computer 60 and could simply be a computer screen attached to or connected to computer 60. Computer 60 is programmed to receive the input as to the user's dimensions and movement being trained and to instruct the display device to display an image identifying for each anchor grouping the specific location on the user at which the distal end of a resistance line connected to the anchor grouping should connect while the user is engaged in the particular body movement. FIG. 13 shows a preferred embodiment system with a display device in the form of projector 70 in electronic communication with computer 60. Based upon the input of dimensional information pertaining to the user, computer 60 instructs projector 70 to project human form image 35 on to panel 202 and overlay the signaling indicators 62. As shown in FIG. 13, human form image 35 would preferably depict a body position to be assumed by the user to begin using the apparatus to train the sport-specific movement. Also, upon being projected upon panel 202, human form image 35 along with the activated anchor indicators would provide graphic indication for each anchor grouping where on the user's body resistance lines emanating from that grouping should attach.

Any of the disclosed embodiments of the present invention systems 1, 101, 201 may further include a harness 17, such as is shown in FIG. 14, that is wearable by the user. Harness 17 includes at least one resistance line receiver 20 to which the distal end 7 of a resistance line 5 may attach. For exercises in which the resistance lines are more advantageously applied via a harness, the printed or projected displays can indicate where on the harness resistance lines should attach. Enhancements to all of the foregoing embodiments include the printed or projected human form image 35 depicting a body position to be assumed by the user to begin using the apparatus to train the sport-specific movement. The present invention is particularly useful for training striking, punching and kicking movements such as are used in boxing, karate, thai boxing, tae kwan do and mixed martial arts. It is also particularly useful for training throwing movements such as pitching or football throwing movements. The apparatus is also useful for training the bat-swinging movement of baseball and the ball-kicking motions as are employed in soccer and American football. Exemplary human form images that may be printed or projected depict body positions for striking, throwing, bat-swinging and ball-kicking are shown in FIGS. 8A-8D. In the example systems of FIGS. 1, 9 and 11 the printed and projected displays show a human form image 35 of a pitcher in a "wind-up" position and denotes which anchors 4 should receive resistance lines 5 to properly train the sport-specific movement.

Figure 15A:
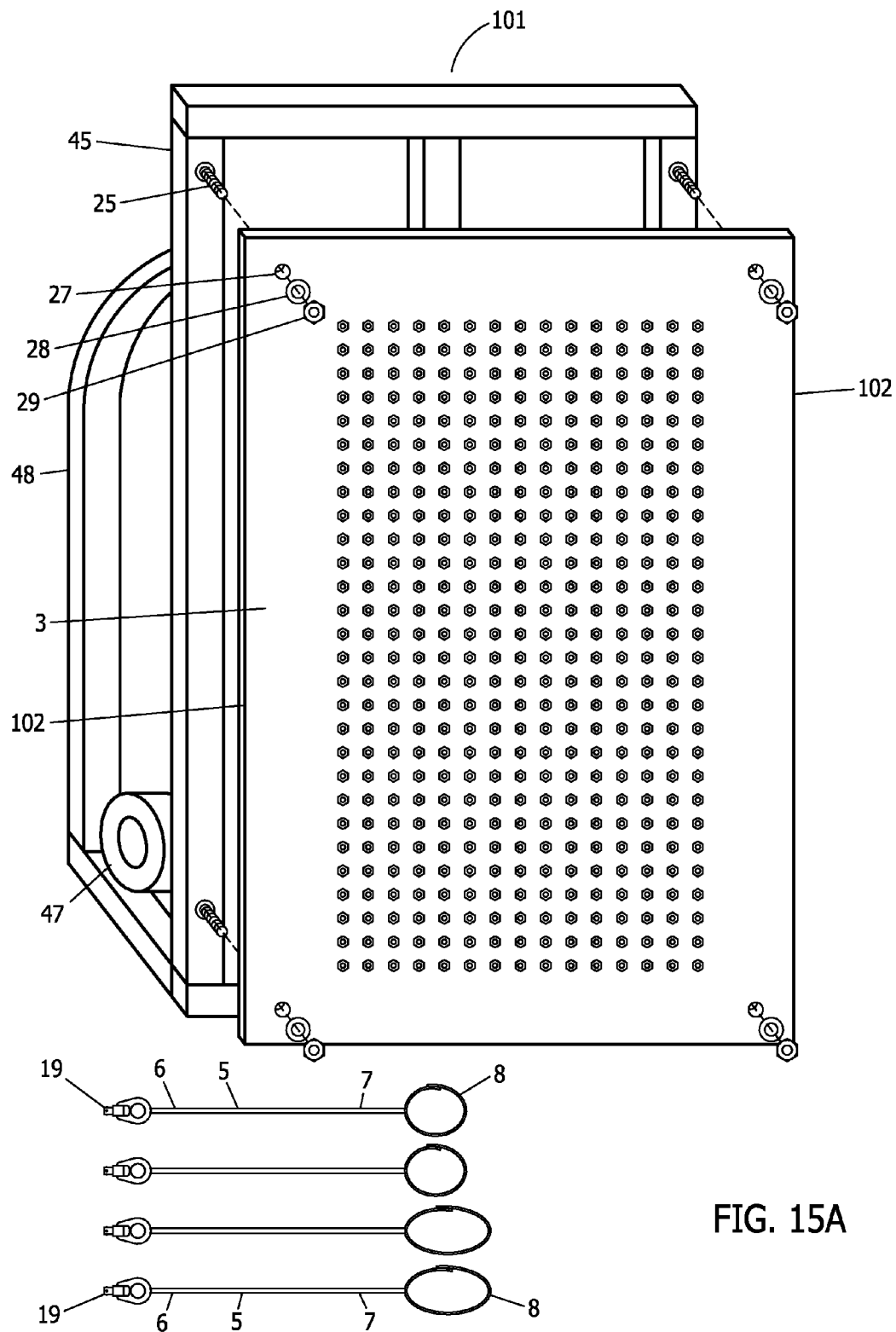
FIGS. 15A-15C depict an exemplary embodiment frame that can be included with any of the embodiment systems discussed in this application.
Figure 15B:
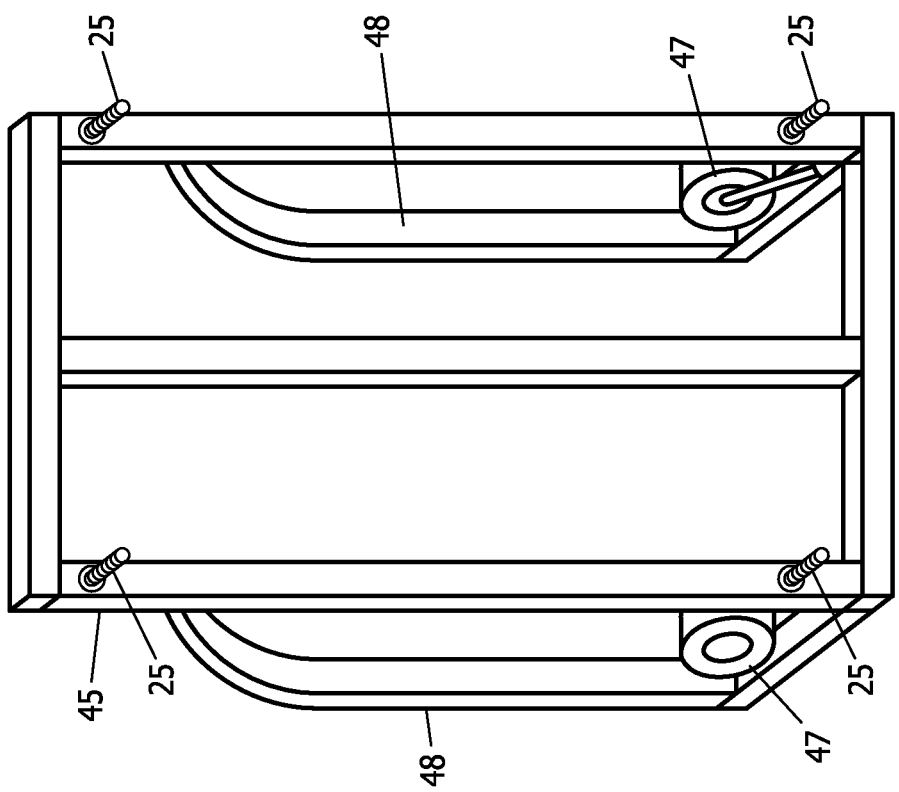
Figure 15C:
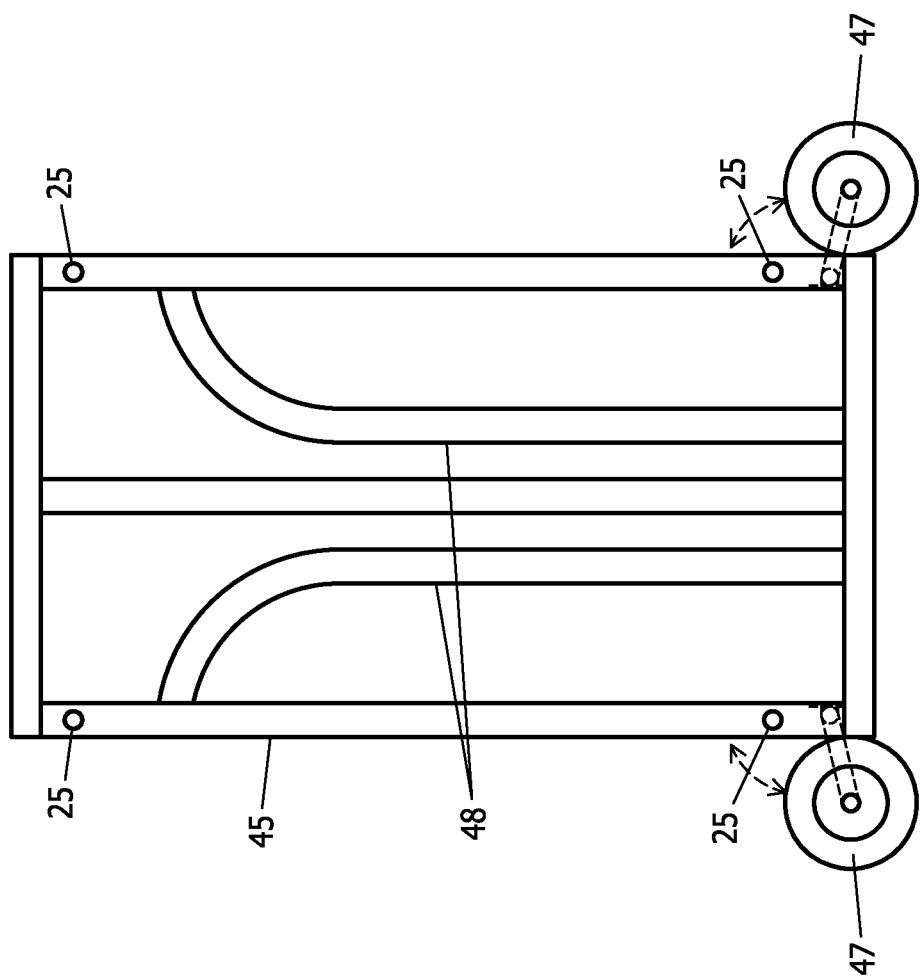

Additionally, any of inventive systems herein described may include a frame to enhance the portability of the systems. An exemplary frame 45 shown in FIGS. 15A, 15B and 15C. Each of panels 2, 102 and 202 are adapted to complementarily engage frame 45 such that any panel may be removably secured to frame 45. Hence, in embodiment, systems 1, 101 and 201, respective panels 2, 102 and 202 include one or more fastener elements that allows the panel to be removably secured, directly or indirectly to frame 45.

Frame 45 is preferably portable such that it can be moved and deployed one or two persons. The same mechanical fastener adaptations (e.g., threaded post 25, hole 27, washer 28 and nut 29 or the fastener elements shown in FIG. 7) such as are described above with respect to the first embodiment being secured to a wall may be used to removably secure panels 2, 102 or 202 to frame 45. In the depicted embodiment, frame 45 includes gated sides 48 and swing-down wheels 47 for portability. Such portability, allows the athlete to utilize resistance training in "field situations." For example, a pitcher wishing to engage in resistance training may desire to train using a regulation pitching mound. In such case, movable frame 45 can be rolled and placed behind a regulation pitching mound.

While preferred embodiments of the present invention have been described, it is to be understood that the embodiments described are illustrative only and that the scope of the invention is to be defined solely by the appended claims.

What is claimed is:

1. A kinetic chain training system for providing resistive force to a user's body while the user is engaged in a particular body movement, the system comprising:
    a panel;
    the panel having a front surface and a plurality of anchors disposed across the front surface of the panel;
    a plurality of elastic resistance lines, each elastic resistance line having a proximal end and a distal end;
    the distal end of each elastic resistance line being adapted to removably connect to one or more locations on the user's body;
    the proximal end of each elastic resistance line being adapted to removably connect to one or more of the plurality of anchors;
    a computer and a printer, the printer being in electronic communication with the computer;
    the computer being programmed to:
        receive input as to a user's body dimensions and the particular body movement engaged in by the user;
        determine one or more anchor groupings, each anchor grouping defining one or more anchors on the panel and each anchor in an anchor grouping being an anchor to which the proximal end of a resistance line attached to a specific location on the user may attach while the user is engaged in the particular body movement; and
        output a signal to the printer instructing the printer to print a sheet;
    the printed sheet being adapted to overlay and removably attach to the front surface of the panel;
    the printed sheet including one or more printed demarcated areas, each demarcated area defining an anchor grouping when the sheet is overlaid on the panel;
    each demarcated area on the printed sheet including holes that allow access through the sheet so as to allow each anchor in an anchor grouping defined by the demarcated area to connect to a resistance line attached to the user when the sheet is in the overlaid position; and
    the printed sheet identifying for each demarcated area the specific location on the user at which the distal end of a resistance line connected to an anchor grouping defined by the demarcated area should connect while the user is engaged in the particular body movement.

2. The system of claim 1 wherein the printed sheet depicts a printed human form image, the human form image defining an area containing the one or more demarcated areas; and
    each demarcated area identifying the location on the user's body at which the distal end of a resistance line connected to an anchor grouping defined by the demarcated area should attach.

3. The system of claim 2 wherein the human form image depicts a body position to be assumed by the user to begin using the apparatus to train the particular body movement.

4. The system of claim 3 wherein the human form image depicts a human form in an act of kicking, throwing, holding a baseball bat or striking.

5. The system of claim 1 further including a harness wearable by the user, the harness including at least one receiver to which the distal end of a resistance line may attach.

6. A kinetic chain training system for providing resistive force to a user's body while the user is engaged in a particular body movement, the system comprising:
    a panel;

the panel having a front surface and a plurality of anchors disposed across the front surface of the panel;

a plurality of elastic resistance lines, each elastic resistance line having a proximal end and a distal end;

the distal end of each elastic resistance line being adapted to removably connect to one or more locations on the user's body;

the proximal end of each elastic resistance line being adapted to removably connect to one or more of the plurality of anchors;

a computer and a projector, the projector in electronic communication with the computer;

the computer being programmed to:
  receive input as to a user's body dimensions and the particular body movement engaged in by the user;
  determine one or more anchor groupings, each anchor grouping defining one or more anchors on the panel and each anchor in an anchor grouping being an anchor to which the proximal end of a resistance line attached to a specific location on the user may attach while the user is engaged in the particular body movement; and
  output a signal to the projector instructing the projector to project an image on the panel;

the projected image including one or more projected demarcated areas, each demarcated area defining an anchor grouping; and the projected image further identifying for each demarcated area the specific location on the user at which the distal end of a resistance line connected to the anchor grouping defined by the demarcated area should connect while the user is engaged in the particular body movement.

7. The system of claim 6 wherein the projected display depicts a human form image, the human form image defining an area containing the one or more demarcated areas; and
  each demarcated area identifying the location on the user's body at which the distal end of a resistance line connected to an anchor grouping defined by the demarcated area should attach.

8. The system of claim 7 wherein the human form image depicts a body position to be assumed by the user to begin using the apparatus to train the particular body movement.

9. The system of claim 8 wherein the human form image depicts a human form in an act of kicking, throwing, holding a baseball bat or striking.

10. The system of claim 6 further including a harness wearable by the user, the harness including at least one receiver to which the distal end of a resistance line may attach.

11. A kinetic chain training system for providing resistive force to a user's body while the user is engaged in a particular body movement, the system comprising:
  a panel in electronic communication with a computer;
  the panel having a front surface and a plurality of anchors disposed across the front surface of the panel;
  each anchor on the panel including an electronically activated indicator integral with or proximate to the anchor;
  a plurality of elastic resistance lines, each elastic resistance line having a proximal end and a distal end;
  the distal end of each elastic resistance line being adapted to removably connect to one or more locations on the user's body;
  the proximal end of each elastic resistance line being adapted to removably connect to one or more of the plurality of anchors;
  the computer being programmed to:
    receive input as to a user's body dimensions and the particular body movement engaged in by the user;
    determine one or more anchor groupings, each anchor grouping defining one or more anchors on the panel and each anchor in an anchor grouping being an anchor to which the proximal end of a resistance line attached to a specific location on the user may attach while the user is engaged in the particular body movement; and
    output a signal to the panel causing the activation of the indicators for the one or more anchors in each of the one or more determined groupings of anchors; and
  a display device in communication with the computer that provides a display that identifies for each anchor grouping the specific location on the user at which the distal end of a resistance line connected to the anchor grouping should connect while the user is engaged in the particular body movement.

12. The system of claim 11 further including a harness wearable by the user, the harness including at least one receiver to which the distal end of a resistance line may attach.

13. The system of claim 11 wherein the display device is a projector;
  the computer being programmed to output a signal to the projector based upon the input received and instruct the projector to project an image on the panel; and
  the projected image further identifying for each anchor grouping the specific location on the user at which the distal end of a resistance line connected to the anchor grouping should connect while the user is engaged in the particular body movement.

14. The system of claim 13 wherein the projected image depicts a human form image, the human form image defining an area containing the one or more anchor groupings; and the location of each determined anchor grouping within the human form image identifying the location on the user's body at which the distal end of a resistance line connected to an anchor grouping should connect while the user is engaged in a particular body movement.

15. The system of claim 14 wherein the human form image depicts a body position to be assumed by the user to begin using the apparatus to train the sport-specific movement.

16. The system of claim 15 wherein the human form image depicts a human form in an act of kicking, throwing, holding a baseball bat or striking.

* * * * *